(12) United States Patent
Blacklin et al.

(10) Patent No.: US 8,312,780 B2
(45) Date of Patent: Nov. 20, 2012

(54) SAMPLING DEVICE AND METHOD

(75) Inventors: Peter Alfred Blacklin, Columbia, MD (US); Wayne Fowler, Jr., Annapolis, MD (US); Joel Michael Hawkins, Old Lyme, CT (US); Howard William Ward, II, Lyme, CT (US)

(73) Assignee: Mettler-Toledo AG, Greifensee (CH)

( * ) Notice: Subject to any disclaimer, the term of this patent is extended or adjusted under 35 U.S.C. 154(b) by 326 days.

(21) Appl. No.: 12/823,718

(22) Filed: Jun. 25, 2010

(65) Prior Publication Data

US 2011/0314900 A1 Dec. 29, 2011

(51) Int. Cl.
*G01N 1/00* (2006.01)

(52) U.S. Cl. ........................................................ 73/863

(58) Field of Classification Search ............... 73/863.82, 73/864.63, 864.73, 864.64, 864.12, 864; 422/521, 119
See application file for complete search history.

(56) References Cited

U.S. PATENT DOCUMENTS

| | | | | |
|---|---|---|---|---|
| 9,239 A | 8/1852 | Winship | ................... | 277/510 |
| 91,007 A | 6/1869 | Fowler | ................... | 285/101 |
| 148,285 A | 3/1874 | Cornelius | ................... | 277/526 |
| 259,449 A | 6/1882 | Woodring et al. | ................... | 277/533 |
| 752,452 A | 2/1904 | Hohmann | ................... | 374/208 |
| 1,460,105 A | 6/1923 | Malone | ................... | 285/279 |
| 1,762,721 A | 6/1930 | Klingner | ................... | 285/342 |
| 2,517,705 A | 8/1950 | Paquin | ................... | 285/342 |
| 2,682,277 A | 6/1954 | Marshall et al. | ................... | 137/334 |
| 2,727,763 A | 12/1955 | Ziep | ................... | 285/342 |
| 2,749,154 A | 6/1956 | Smith | ................... | 285/309 |
| 3,179,448 A | 4/1965 | Jones | ................... | 285/123.6 |
| 3,207,233 A | 9/1965 | Shumaker | ................... | 172/316 |
| 3,323,874 A | 6/1967 | Phillips | ................... | 422/538 |
| 3,541,860 A | 11/1970 | George | ................... | 73/863.83 |
| 3,544,281 A | 12/1970 | Phillips | ................... | 422/545 |
| 3,656,349 A | 4/1972 | Collins, Jr. | ................... | 73/864.34 |
| 3,695,642 A | 10/1972 | DeWoody | ................... | 285/148.3 |
| 3,719,086 A | 3/1973 | Bannister et al. | ................... | 73/864.22 |
| 3,747,411 A | 7/1973 | McDermott et al. | ................... | 73/863.54 |
| 3,807,233 A | 4/1974 | Crawford | ................... | 73/863.11 |
| 3,852,512 A | 12/1974 | Herrmann, Jr. | ................... | 174/19 |
| 4,147,062 A | 4/1979 | Jaeger | ................... | 73/863.83 |
| 4,262,533 A | 4/1981 | Jaeger | ................... | 73/863.11 |
| 4,346,609 A | 8/1982 | Diesel | ................... | 73/863.84 |
| 4,475,410 A | 10/1984 | Jaeger | ................... | 73/863.84 |

(Continued)

FOREIGN PATENT DOCUMENTS

CA 2345838 A1 7/2002

(Continued)

*Primary Examiner* — Peter J Macchiarolo
*Assistant Examiner* — Tamiko Bellamy
(74) *Attorney, Agent, or Firm* — Standley Law Group LLP

(57) ABSTRACT

An in situ autosampling method and associated sampling device for capturing a material sample from a vessel. Methods of the present invention make use of a sampling device having an extendable sample capture element with a concave sample capture pocket located near a distal end thereof. The sample capture pocket is adapted to capture a known volume of material when the sample capture element is extended into said material. The material sample remains trapped in the sample capture pocket upon sample capture element retraction. Ports in the sample capture pocket may be placed in communication with corresponding material transfer channels extending through the sample capture element to allow for the in situ processing of a material sample, and the subsequent discharge of the sample to an analyzer or another downstream location.

31 Claims, 15 Drawing Sheets

U.S. PATENT DOCUMENTS

| | | | |
|---|---|---|---|
| 4,635,470 A | 1/1987 | Skallen et al. | 73/53.04 |
| 4,669,763 A | 6/1987 | Phillips | 285/346 |
| 4,744,255 A | 5/1988 | Jaeger | 73/863.84 |
| 4,846,970 A | 7/1989 | Bertelsen et al. | 210/232 |
| 4,886,304 A | 12/1989 | Kunsman | 285/104 |
| 4,891,104 A | 1/1990 | Liston et al. | 204/403.05 |
| 4,957,706 A | 9/1990 | Romette et al. | 422/510 |
| 5,109,708 A | 5/1992 | Lawless | 73/863.11 |
| 5,384,095 A | 1/1995 | Golz et al. | 422/501 |
| 5,404,760 A | 4/1995 | Robinson et al. | 73/863.11 |
| 5,454,912 A | 10/1995 | Dougherty | 162/263 |
| 5,905,213 A | 5/1999 | Jaeger | 73/863.85 |
| 6,055,870 A | 5/2000 | Jaeger | 73/863.83 |
| 6,178,830 B1 | 1/2001 | Freud | 73/863.51 |
| 6,357,306 B1 | 3/2002 | Jaeger | 73/863.83 |
| 6,520,343 B2 | 2/2003 | Karlsson et al. | 210/409 |
| 6,860,162 B1 | 3/2005 | Jaeger | 73/863.85 |
| 6,874,354 B2 | 4/2005 | Cueni et al. | 73/61.55 |
| 6,918,310 B2 | 7/2005 | Bjork et al. | 73/863.81 |
| 7,160,511 B2 | 1/2007 | Takahashi et al. | 422/504 |
| 7,213,474 B2 | 5/2007 | Bjork et al. | 73/863.81 |
| 7,389,792 B2 | 6/2008 | Newberg | 137/551 |
| 7,472,615 B2 | 1/2009 | Mayeaux | 73/866.5 |
| 7,481,124 B2 | 1/2009 | Schadt | 73/863.86 |
| 7,753,857 B2 | 7/2010 | Hibner | 600/566 |
| 7,758,515 B2 | 7/2010 | Hibner | 600/566 |
| 2003/0188588 A1 | 10/2003 | Jaeger | 73/863.84 |
| 2004/0016460 A1 | 1/2004 | Newberg | 137/551 |
| 2004/0055402 A1 | 3/2004 | Pensis et al. | 15/353 |
| 2005/0229727 A1 | 10/2005 | Caderas | 73/866.5 |
| 2005/0284239 A1* | 12/2005 | Chuang | 73/864 |
| 2006/0074345 A1 | 4/2006 | Hibner | 600/566 |
| 2008/0022753 A1 | 1/2008 | MacPherson et al. | 73/31.01 |
| 2008/0190218 A1 | 8/2008 | Riazanskaia et al. | 73/864 |
| 2009/0038419 A1 | 2/2009 | Hiller et al. | 73/864.73 |
| 2009/0145205 A1 | 6/2009 | Hochgraeber et al. | 73/61.55 |
| 2010/0228146 A1 | 9/2010 | Hibner | 600/566 |
| 2011/0189713 A1 | 8/2011 | Le Comte et al. | 435/29 |

FOREIGN PATENT DOCUMENTS

| | | |
|---|---|---|
| CH | 544302 A | 11/1973 |
| CN | 201166619 Y | 12/2008 |
| DE | 1914118 A1 | 10/1970 |
| DE | 3836826 A1 | 5/1989 |
| DE | 20103617 U1 | 4/2001 |
| WO | 98/39630 A1 | 9/1998 |
| WO | 00/38837 A1 | 7/2000 |
| WO | 01/16460 A1 | 3/2001 |
| WO | 03/095087 A1 | 11/2003 |

\* cited by examiner

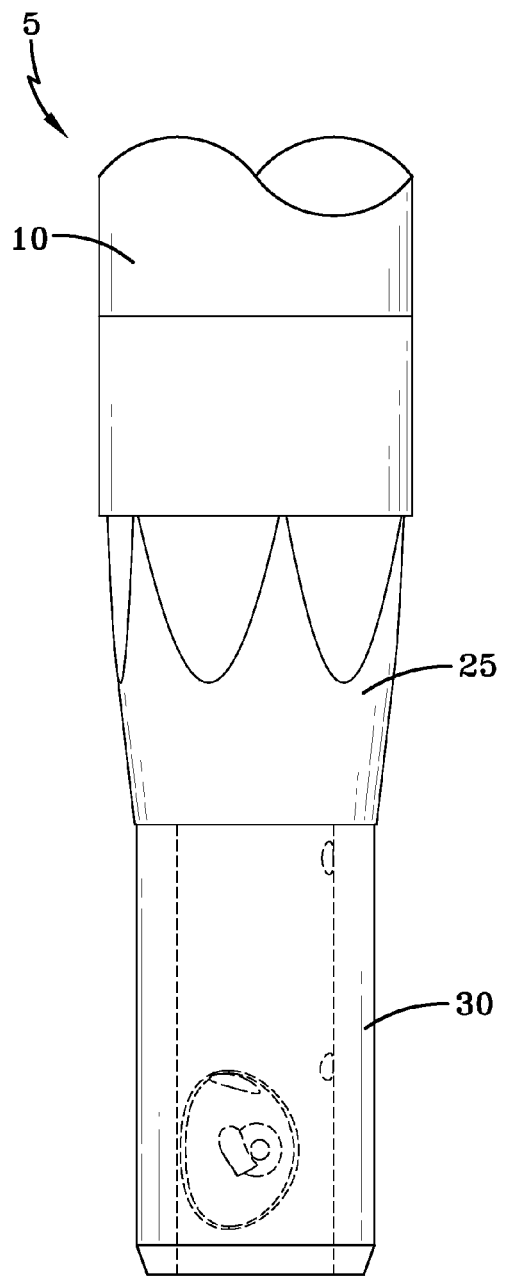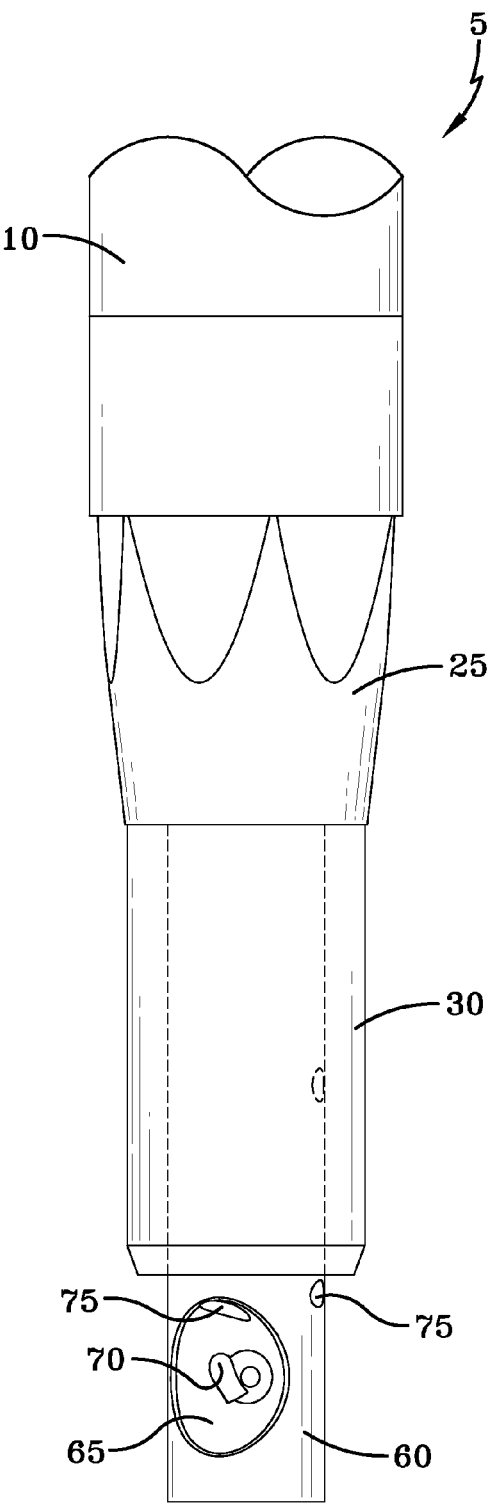
FIG-2a
FIG-2b

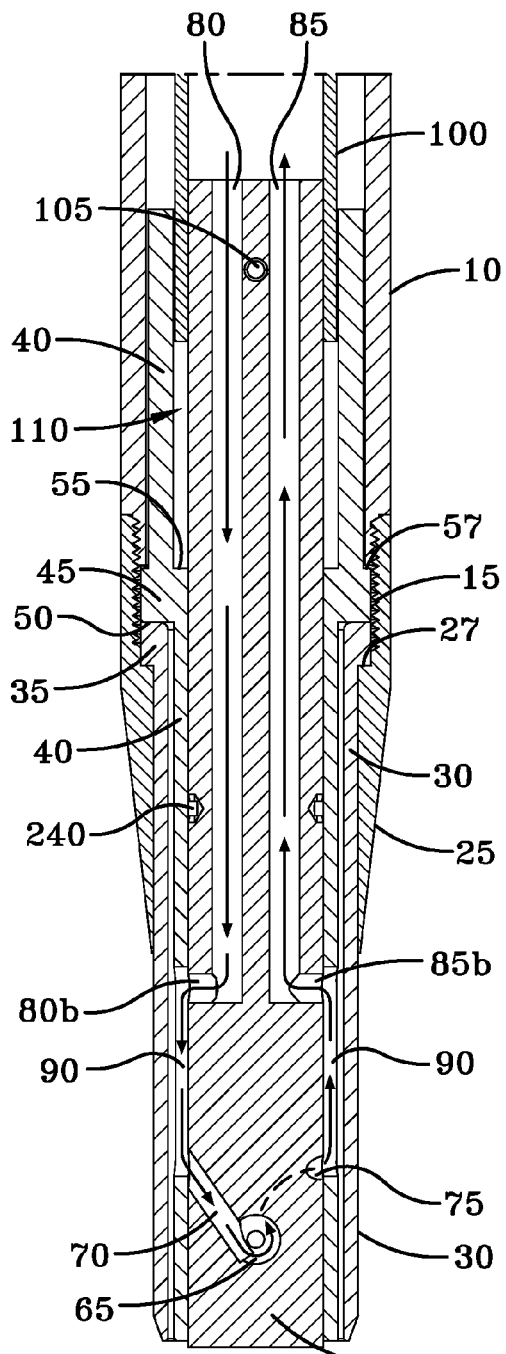
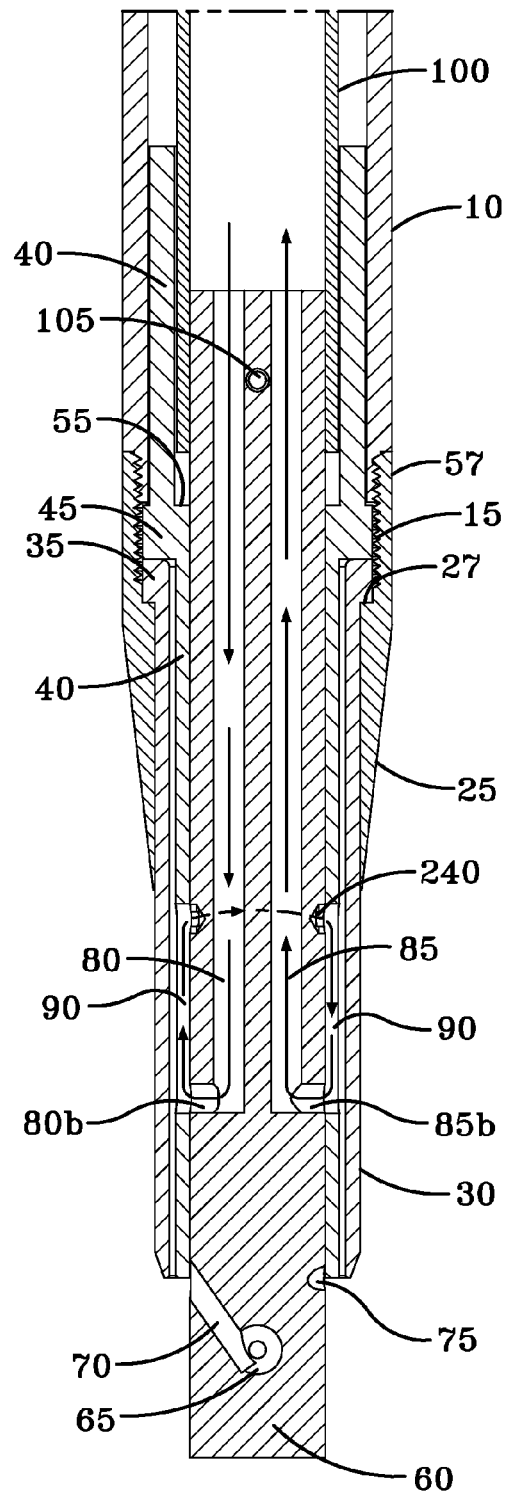
FIG-4a
FIG-4b

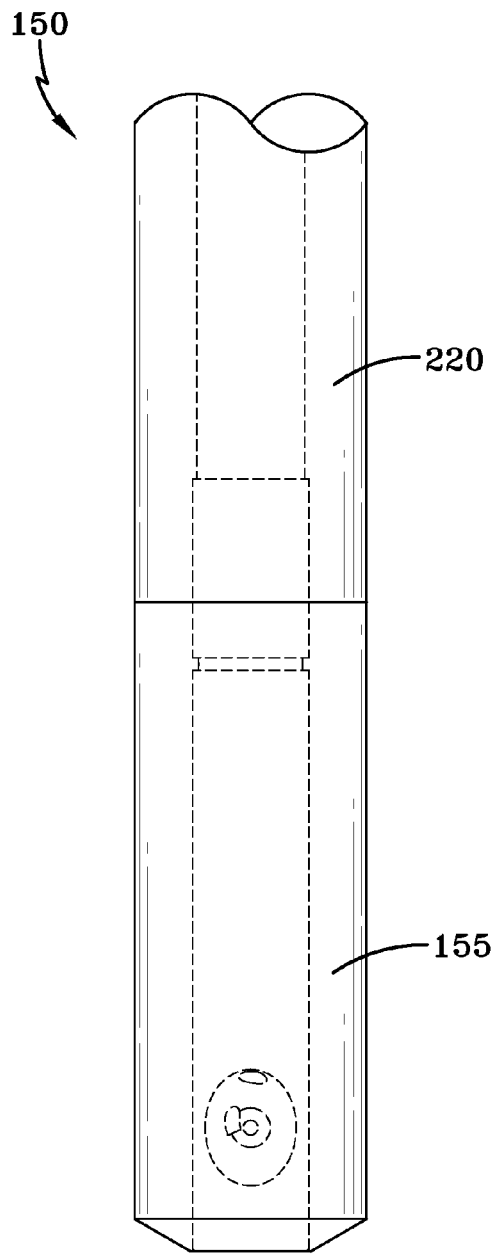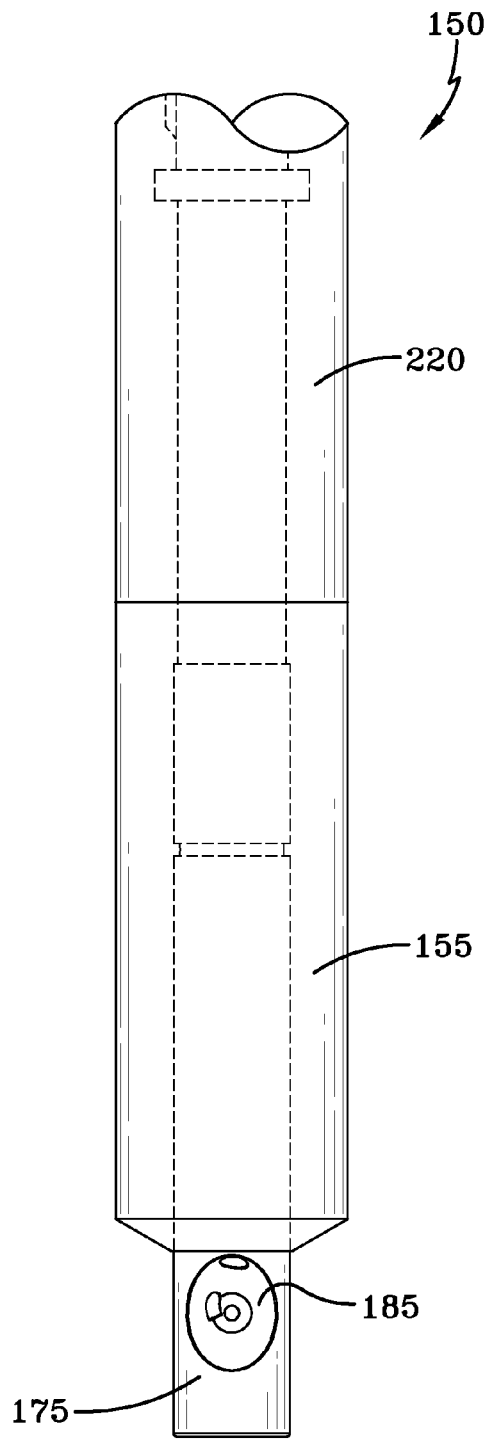
FIG-6a
FIG-6b

SAMPLING DEVICE AND METHOD

TECHNICAL FIELD

The present invention is directed to a device and method for acquiring a material sample. More particularly, the present invention is directed to a method of acquiring a material sample, such as reaction/reactant sample, using a sampling device having an extendable sample capture element.

BACKGROUND

As would be obvious to one of skill in the art, there are a number of situations and/or processes for which it would be desirable to extract a sample of a material from a vessel in which the material is contained. Such extraction would generally be desirable for purposes of examination or testing, but could be performed for other reasons, as well.

With respect to process monitoring, such sample extraction may be desirable in a number of processes, including without limitation, parallel synthesis (combinatorial chemistry) applications, organic synthesis, chemical process development, and the scale-up of laboratory processes into production. A number of other such applications wherein sample extraction would be of interest also exist and would be known to those of skill in the art.

Known sampling devices may be operated by hand, or may employ a vacuum-based device mounted remotely or in a vessel containing a material of interest, or a by-pass port or similar mechanism through which amount of a material of interest can be siphoned. In any case, however, known methods generally require that an extracted sample be removed from the vessel and then transferred to another container before the sample can be quenched or similarly operated upon.

Known manual sample capture and analysis methods commonly suffer from a lack of precision with regard to the timing of sample capture and subsequent sample processing. Further, sample capture methods can only be used to take samples that are at atmospheric pressure. Reactions that take place under pressure cannot be sampled by these techniques. A sample capture method that makes use of a by-pass type of sampling device, where the reaction flows through a loop to a point where it can be sampled, can be used to sample reactions under pressure—however, a large reaction volume is required to use such a device.

Importantly, known sample capture methods also do not permit sample processing (mixing, quenching, dilution, etc.), to take place substantially contemporaneously with sample capture but, rather, require that a sample be first transferred to another vessel. Consequently, the state of a given sample may actually change from the time of sample extraction to the time of quenching, etc.

Therefore, based on these foregoing issues with known sampling methods, it should be apparent that a method for capturing a material sample and for processing the material sample in situ and substantially contemporaneously with sample capture would be desirable. A sample capture device and method of the present invention allows for such a process.

SUMMARY OF THE GENERAL INVENTIVE CONCEPT

Embodiments sampling devices that may be used according to the present invention may be disposed as elongate probes having extendable sample capture elements. Among other things, a sampling device of the present invention may be used to sample small reaction volumes (e.g., 5-100 µl), and to extract a sample from within a reaction volume. Because a sampling device of the present invention is a sealed unit, it can also be placed through a port into a pressurized or evacuated reaction chamber to sample a pressurized reaction volume. A sampling device of the present invention may also be used throughout a wide temperature range (e.g., −40° C.-150° C.).

Unlike known sample capture methods, methods of the present invention allow for substantially contemporaneous sample capture and sample processing (e.g., quenching, diluting mixing, etc.). Therefore, practicing the present invention minimizes or eliminates any change in sample conditions between the time of sample capture and sample processing. This is not possible with devices or methods currently known to the inventors.

In one embodiment, a sampling device of the present invention may include a substantially cylindrical and hollow outer tube of some length. A proximal end of the outer tube may be clamped or otherwise affixed to a body portion of a probe actuator assembly. Concentrically arranged within the outer tube at a distal end thereof is an assembly including an outer sleeve, an inner sleeve and an extendable sample capture element. A substantially frustoconical adapter is attached to the distal end of the outer tube and tapers to a reduced diameter that approximates the diameter of the outer sleeve.

Both the outer sleeve and the inner sleeve are held in position by the adapter, which presses an upper shoulder of the inner sleeve collar tightly against the distal face of the outer tube when attached thereto. Consequently, when the adapter is fully assembled to the outer tube, the inner sleeve and the outer sleeve are held tightly together and are also prevented from movement with respect to the outer tube and the adapter.

The sample capture element is located to reciprocate within the inner sleeve. The outer diameter of the sample capture element is provided to be close in dimension to the inner diameter of the inner sleeve, such that a tight but slidable fit is produced therebetween. When the sample capture element is in a retracted (closed) position, the distal end thereof may be positioned substantially even with the distal ends of the inner porting sleeve and the outer sleeve. When the sample capture element is in an extended (sampling) position, the distal end thereof may protrude from the distal end of the outer sleeve. The sample capture element is provided with a concave sample capture pocket that, during sample capture element extension, is exposed to and captures an amount of a sample of interest.

A proximal portion of the sample capture element extends into the enlarged inner diameter of the proximal portion of the inner sleeve. The proximal end of the sample capture element is received within the distal end of a substantially hollow inner tube that is concentrically arranged within the outer tube. The outer diameter of the inner tube approximates the inner diameter of the proximal portion of the inner porting sleeve such that a tight but slidable fit is produced therebetween. The sample capture element is retained in the inner tube, such as by a pin.

In an exemplary automated (autosampling) embodiment of a device of the present invention, a proximal end of the inner tube extends through the proximal end of the outer tube and is connected to an actuator (e.g., pneumatic cylinder) that provides the desired extension and retraction of the sample capture element. In an exemplary hand-actuated (manual) embodiment of a device of the present invention, the inner tube may be similarly connected to a hand-operable lever mechanism or linearly-driven plunger that provides the desired extension and retraction of the sample capture element when manually actuated by a user of the device.

During extension and retraction of the sample capture element, the sample capture element is guided by contact between its exterior and the interior of distal portion of the inner porting sleeve, as well as by contact between the exterior of the inner tube and the interior of the proximal portion of the inner porting sleeve. Proper linear movement of the sample capture element is thus ensured. Rotation of the sample capture element during reciprocation may be prevented if desired.

The sample capture element is ported to allow for purging/venting and to allow for the in situ processing (mixing, dilution, quenching, etc.), of material samples while located in the sample capture pocket thereof. Particularly, the sample capture pocket is provided with a supply port and a purge/vent port, each of which is associated with a corresponding channel that runs through the sample capture element and exits through the proximal end thereof. Sample lines (e.g., tubing) may be connected to each of these supply and purge/vent channels to lead processing materials to the sample capture pocket and to allow for venting and for material to be purged from the sample capture pocket. Such tubing may be routed through the inner tube. The distal portion of the inner sleeve is provided with porting slots that allow the ports in the sample capture pocket to communicate with the corresponding channels in the sample capture element during a processing (e.g., mixing, dilution, quenching) or purge/vent cycle.

In another exemplary embodiment, the above-described design may be altered to have a fewer number of individual components. Particularly, in this alternative embodiment, the inner and outer sleeves and the adapter of the previously described embodiment are combined into a single element. This element forms an end cap that threads into the distal end of an outer tube and acts as a reciprocation guide and protective cover for the sample capture element. The end cap contains interior channels or grooves that connect the ports of the sample capture pocket of the sample capture element to the channels of the sample capture element.

During use of either of these embodiments, the distal end of the device is typically immersed in or held near the surface of a material from which a sample is to be extracted. At the desired time, the sample capture element is extended into the material, whereby an amount of the material fills the sample capture pocket and remains therein as the sample capture element is subsequently retracted back into the closed position. With the sample of material trapped in the sample capture pocket, the sample may be processed, such as by contacting the sample with a quenching or diluting substance so as to halt an ongoing reaction or dilute the sample, prior to transferring the sample of material to another device or vessel.

When a sample capture element of a sampling device of the present invention is extended into a reaction volume to capture a sample, the sample lines are typically empty, having been purged for example, with a gas or with a liquid that is neutral to the reaction being sampled. As should be apparent, when the sample capture element extends into the reaction volume, any material inside the sample capture pocket will come into contact with the reaction materials.

The choice of purge material may vary depending on the reaction being sampled. For example a gaseous purge material may not be ideal if the reaction volume is small and the reaction is under pressure, as the purge gas may cause a fluctuation in the reaction pressure. Similarly, any fluid present in the sample capture pocket when the sample capture element extends will quickly mix with the reaction materials. It must also be considered that remnants of any quench media could compromise a reaction.

While the sample capture element is extended, the sample lines that were previously empty, may be filled with quench media. The flow path through the sampling device may include transfer ports and a by-pass groove in the sample capture element to allow flow in the fluid circuit when the sample capture element is in an extended position.

In the case of the aforementioned exemplary embodiments, the porting slots of the inner sleeve (or combined element) align with the sample capture element transfer ports as the sample capture element reaches full extension, allowing flow through the bypass groove and channels and within the sample line circuit. Quench media may, therefore, be introduced to the sample capture element and possibly placed under pressure while the sample capture element is still extended. In this manner, quench media is available to immediately flow into the sample capture pocket and mix with the captured material sample upon retraction of the sample capture element and alignment of the sample capture pocket ports with the porting slots of the inner sleeve.

Therefore, unlike known devices and methods, sample processing according to the present invention may occur while the captured sample is still in the sampling device (i.e., in situ). Further, by providing a waiting supply of quench media or other material, sample processing can be initiated immediately upon retraction of the sample capture element. This ensures that the captured sample is preserved in a condition that is as close as possible to the condition of the sample volume from which it was extracted.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 2*a* is an enlarged view in partial transparency of a distal portion of the autosampling device of FIG. 1 with a sample capture element thereof in a retracted (closed) position;

FIG. 2*b* shows the distal portion of the autosampling device of FIG. 2*a* with the sample capture element thereof in an extended (sampling) position;

FIG. 4*a* is an enlarged cross-sectional view of the distal portion of the autosampling device of FIG. 1, wherein the sample capture element thereof is in a retracted (closed) position and a first (collection mode) liquid flow path is shown;

FIG. 4*b* shows the distal portion of the autosampling device of FIG. 4*a* with the sample capture element thereof in an extended (sampling) position and a second (bypass mode) liquid flow path is shown;

FIG. 6*a* shows an assembled distal portion of an alternate exemplary embodiment of an autosampling device of the present invention, with an associated sample capture element thereof in a retracted (closed) position;

FIG. 6b shows the autosampling device of FIG. 5a with the sample capture element thereof in an extended (sampling) position;

FIG. 9b is an enlarged view of a portion of the sample capture element and sleeve of FIG. 9a;

FIG. 10b is an enlarged view of a portion of the sample capture element and sleeve of FIG. 10a;

DETAILED DESCRIPTION OF EXEMPLARY EMBODIMENT(S)

One exemplary embodiment of a sampling device 5 of the present invention is illustrated in FIGS. 1-5. In this case, the device is an autosampling device 5, as explained in more detail below. However, such a design may also be substantially used in a hand-actuated (manual) version of a sampling device according to the present invention. A partial inventory of the components of this device 5 are illustrated in the exploded view of FIG. 1.

Figure 5:
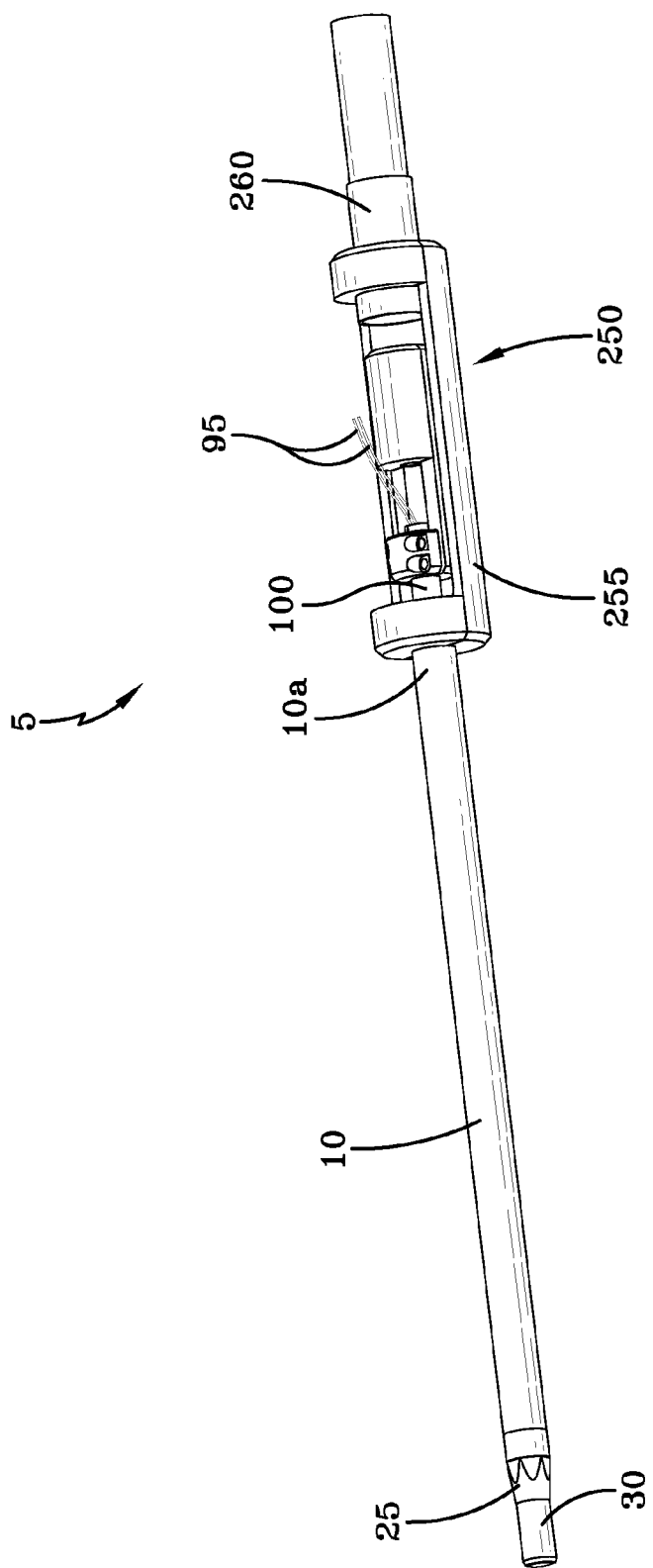
FIG. 5 depicts the sample capture device of FIGS. 1-4*b* in a fully assembled condition.

As shown, this autosampling device 5 includes a substantially cylindrical and hollow outer tube 10 of some desired length. A proximal end 10a of the outer tube 10 may be clamped or otherwise affixed to a body portion 255 of a probe actuator assembly 250, as shown in FIG. 5. A distal end 10b of the outer tube 10 is threaded as shown. In this case, the threads 15 are externally disposed on the outer tube 10, although internal threading may be provided in other embodiments. The outer tube 10 may be constructed from various materials depending on the substances to which it might be exposed. It has been found, however, that a HASTELLOY alloy, such as HASTELLOY C-22 or C-276, is particularly well-suited for this purpose. HASTELLOY alloys are available from Haynes International, Inc.

Concentrically arranged within a distal portion of the outer tube 10 is a sample capture assembly 20 that includes an outer sleeve 30, an inner sleeve 40, an extendable sample capture element 60, and a clamping adapter 25.

The clamping adapter 25 of this particular autosampling device 5 is substantially frustoconical in shape, with a proximal portion 25a of larger diameter than a distal portion 25b thereof. The proximal end of the adapter 25 is internally threaded to engage the threaded distal end 10b of the outer tube 10. External threading may be provided in other embodiments having an internally threaded outer tube. Preferably, but not essentially, the adapter 25 of this autosampling device 5 is constructed from the same material as the outer tube 10.

The outer sleeve 30 is constructed as a elongate hollow tube of some length, with a collar 35 of enlarged diameter encircling its external proximal end 30a. The outer sleeve 30 is received in the adapter 25 and positioned therein by contact of a lower shoulder formed by the collar 35 of the outer sleeve 30 and a corresponding shoulder 27 formed in the adapter (see FIGS. 4a-4b). In this embodiment of the autosampling device 5, a distal portion 30b of the outer sleeve 30 extends through the reduced diameter opening in the adapter and protrudes therefrom by some predetermined distance. Preferably, the inner diameter of the distal portion 25b of the adapter 25 and the outer diameter of the outer sleeve 30 portion that passes therethrough are of dimensions that produces a slip fit therebetween.

The outer sleeve 30 may be constructed from various materials depending on the materials to which it might be exposed. In this particular embodiment, the outer sleeve 30 is constructed of stainless steel.

The inner sleeve 40 is also constructed as a elongate hollow tube of some length. The inner sleeve 40 includes a proximal portion 40a having an inner and outer diameter that is greater than the inner and outer diameter of a distal portion 40b thereof. The distal and proximal portions 40a, 40b of the inner sleeve 40 are separated by a collar 45 that forms a lower exterior shoulder 50 and upper interior and exterior shoulders 55, 57. The distal portion 40b of the inner sleeve 40 is received and resides within the interior of the outer sleeve 30. The outer diameter of the distal portion 40b of the inner sleeve 40 and the inner diameter of the outer sleeve 30 are each of a dimension that results in a sealing fit therebetween.

As shown in FIGS. 4a-4b, the longitudinal position of the inner sleeve 40 within the outer sleeve 30 is set by contact between the bottom shoulder 50 of the inner sleeve collar 45 and the proximal end 30a and collar 35 of the outer sleeve 30. Preferably, the length of the distal portion 40b of the inner sleeve 40 is such that the distal ends of the inner sleeve and outer sleeve 30 are aligned when the inner sleeve is installed in the outer sleeve.

The inner sleeve 40 may be constructed from various materials depending on the substances to which it might be exposed. In this particular embodiment, the inner sleeve 10 is constructed of a polytetrafluoroethylene (PTFE) material, such as a TEFLON material available from DuPont. An advantage to using a material such as TEFLON is that it is inert to most chemicals and has a low coefficient of friction.

It has also been found that the natural elasticity of PTFE allows it to create a good seal between the outer sleeve 30 and a sample capture element 60 of the autosampling device 5. More particularly, the elastic-plastic behavior of such a material allows normal tight manufacturing tolerances to be applied. In this case, the bore of the inner sleeve 40 may be made smaller than the outer diameter of a sample capture element 60 described in more detail below) that reciprocates therein, yet when the two components are fitted together the TEFLON yields at the inside bore and burnishes (i.e., the local yielding polishes the internal surface of the inner sleeve) during installation. Preferably, the inner diameter of the sleeve 40 is selected to maintain the external fibers in the elastic state (until higher temperatures are reached) so that the sleeve provides a compressive sealing force against the sample capture element, thereby sealing the passages and transfer passages from communicating with adjacent passages.

When the adapter 25 and the inner and outer sleeves 30, 40 are installed to the distal end 10b of the outer tube 10, the larger diameter proximal portion 40a of the inner sleeve 40 extends into the distal end of the outer tube 10. The outer diameter of the proximal portion 40a of the inner sleeve 40 and the inner diameter of the outer tube 10 are each of a dimension that preferably results in a sealing fit therebetween.

Both the outer sleeve 30 and the inner sleeve 40 are held in position by the adapter 25, which presses the upper outer shoulder 57 of the inner sleeve collar 45 tightly against the distal face of the outer tube 10 when the adapter is threaded onto the outer tube. The adaptor 25 acts as a clamping means to retain the outer sleeve 30 and the inner sleeve 40 and to seal the outer tube 10 with the collar 45 of the inner sleeve collar 40. Concurrently, the inner sleeve 40 and the outer sleeve 30 are also held tightly together and are prevented from longitudinal (linear) movement with respect to the outer tube 10 and the adapter 25.

As mentioned above, the sample capture assembly 20 also includes a sample capture element 60. The sample capture element 60 is located to reciprocate within the inner sleeve 40, as can be best understood by reference to FIGS. 2a-2b and 4a-4b. To that end, the outer diameter of the sample capture element 60 and the inner diameter of the distal portion 40b of the inner sleeve 40 are of a dimension that produces a sealing but guided slidable fit therebetween.

The length of the sample capture element 60 may vary depending on the length of the outer tube 10 and/or other components of the autosampling device 5. Preferably, the length of the sample capture element 60 is at least sufficient such that the proximal end thereof resides in the interior of the proximal portion 40a of the inner sleeve 40, whether the sample capture element 60 is in an extended or retracted position.

When the sample capture element 60 is in a retracted (closed) position, as shown in FIGS. 2a and 4a, the distal end 60b thereof is preferably positioned substantially evenly with the distal ends of the inner sleeve 40 and the outer sleeve 30. When the sample capture element 60 is in an extended (sampling) position, as shown in FIGS. 2b and 4b, the distal end 60b thereof protrudes from the distal ends of the inner sleeve 40 and the outer sleeve 30 by some predetermined distance.

Figure 1:
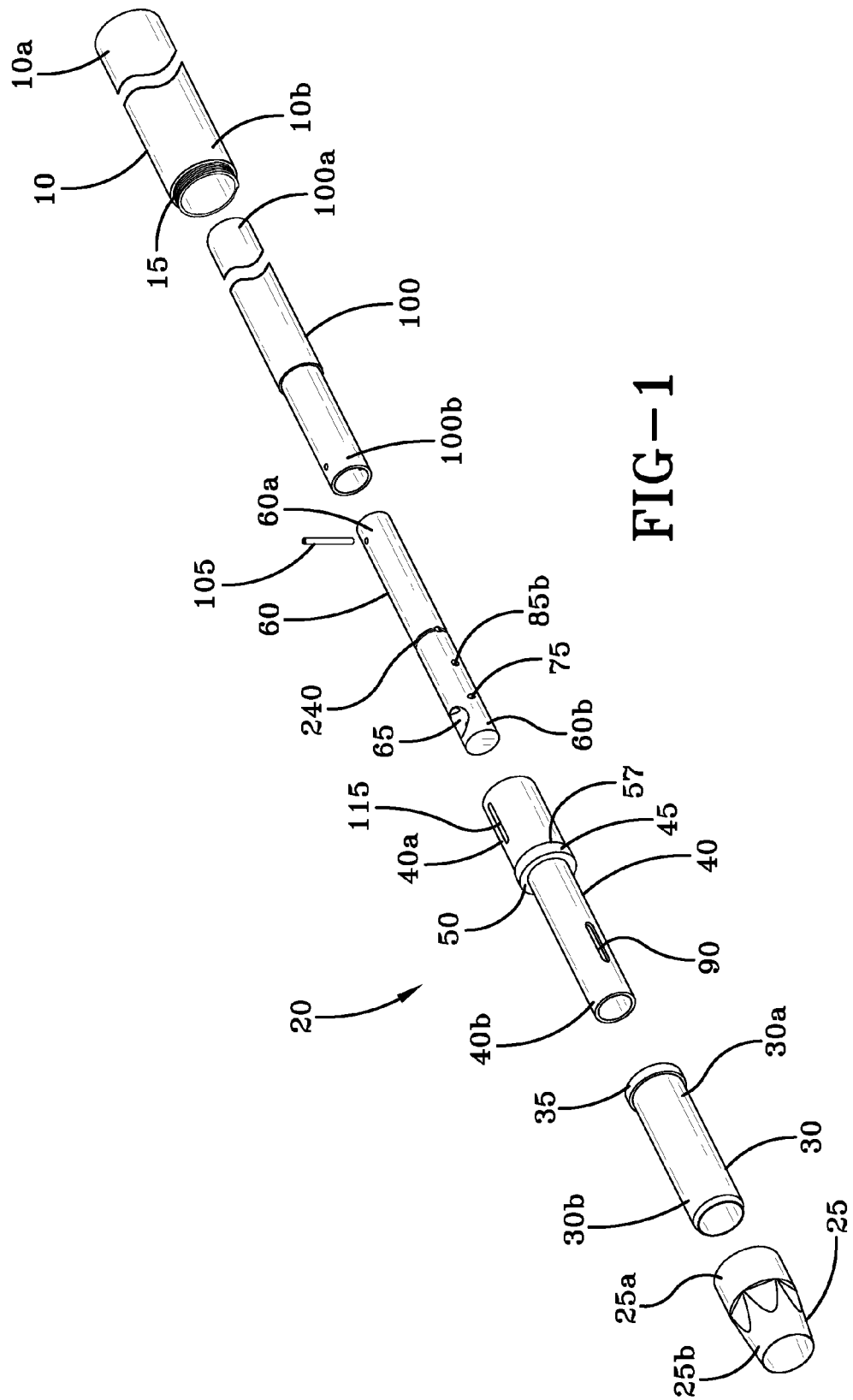
FIG. 1 is an exploded view of a portion of one exemplary embodiment of an autosampling device of the present invention.
Figure 3:
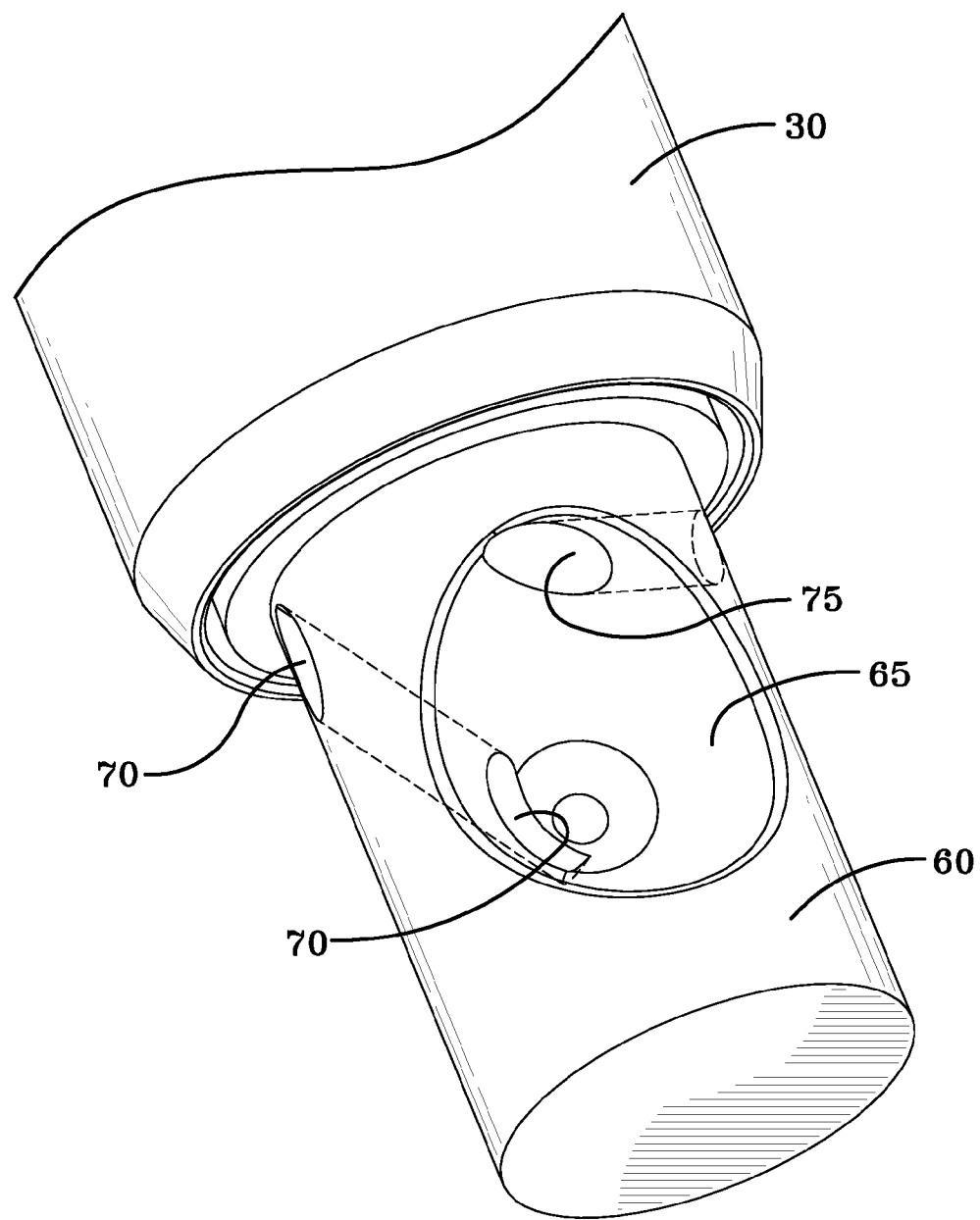
FIG. 3 is an enlarged view of a distal end of an exemplary sample capture element of the present invention, wherein a ported sample capture pocket is visible.

As most clearly shown in FIG. 3, the sample capture element 60 is provided with a concave sample capture pocket 65 that, during sample capture element extension, is exposed to and captures an amount of a sample in which the distal end of the autosampling device 5 is immersed. The sample capture pocket 65 may be provided in different sizes to capture different sample volumes (aliquots).

The sample capture element 60 may be constructed from various materials depending on the substances to which it might be exposed. In this particular embodiment, the sample capture element 60 is constructed of a ceramic material. Sample capture elements of embodiments of the present invention may be resistant to strong acids and strong caustics.

The sample capture element 60 is ported to allow for purging/venting and to allow for quenching of material samples located in the sample capture pocket 65 thereof. Particularly, the sample capture pocket 65 is provided with a quench port 70 and a purge/vent port 75, each of which is associated with a corresponding channel 80, 85 that runs through the sample capture element 60 and exits through the proximal end 60a thereof. The distal portion 40b of the inner sleeve 40 is provided with porting slots 90 that allow the ports 70, 75 in the sample capture pocket 65 to communicate with the corresponding channels 80, 85 in the sample capture element 60 during a quenching or purge/vent cycle.

The sample capture element 60 may also be provided with a by-pass groove 240 that is placed in fluid communication with transfer ports 80b, 85b of the channels 80, 85 in the sample capture element by the porting slots 90 in the inner sleeve 40 to permit circulation of a quench media while the sample capture element is in an extended position. This allows sample lines and the channels 80, 85 in the sample capture element 60 to be filled with recirculating quench media as illustrated in FIG. 4b. Quench media may, therefore, be introduced to the sample capture element 60 and possibly placed under pressure while the sample capture element is in an extended position. In this manner, quench media is available to immediately flow into the sample capture pocket 65 and mix with a captured sample upon retraction of the sample capture element and alignment of the sample capture pocket ports 70, 75 with the porting slots 90 of the inner sleeve.

As shown in FIG. 5, tubing 95 or similar conduit may be connected to each of the quench and purge/vent channels 80, 85 to lead quench materials to the sample capture pocket 65, and to allow for venting and for material to be purged from the sample capture pocket. When flexible plastic tubing is used for this purpose, ends of the tubing 95 may be pre-formed with threads by techniques known to those of skill in the art, the threaded ends may be subsequently trimmed to provide a uniform face to the threaded tube end, and the threaded ends of the tubing may be engaged with like threaded sections provided in the proximal ends of the channels 80, 85. Upon threading the tubing into the associated channels in the sample capture element, the threaded ends of the tubing bottom out on the pilot diameter of the channels, thereby producing a seal. Such tubing 95 may be routed through an inner tube 100 (described in more detail below) of the autosampling device 5.

The proximal end 60a of the sample capture element 60 extending into the interior of the proximal portion 40a of the inner sleeve 40 is received within the distal end 100b of a substantially hollow inner tube 100 that is concentrically arranged within the outer tube 10. As best shown in FIGS. 4a-4b, the outer diameter of the inner tube 100 approximates the inner diameter of the proximal portion 40a of the inner sleeve 40, such that a sealing but slidable fit is produced therebetween.

In this embodiment, the proximal end 60a of the sample capture element 60 is retained in the distal end 100b of the inner tube 100 by a pin 105 that passes through corresponding holes in both components. As shown in FIG. 5, the proximal end 100a of the inner tube 100 extends through the proximal end 10a of the outer tube 10 and is connected to an actuator 260 that provides the desired extension and retraction of the sample capture element 60.

Referring to FIG. 4a, it can be observed that when the sample capture element 60 is in a retracted position, a gap 110 exists between the distal end 100b of the inner tube 100 and the upper inner shoulder 55 of the inner sleeve 40. The length of this gap 110 represents the maximum possible length of extension of the sample capture element 60 because, as shown in FIG. 4b, contact between the distal end 100b of the inner tube 100 and the upper inner shoulder 55 of the inner sleeve 40 will function as a hard stop with respect to sample capture element 60 extension. Of course, the actuator 260 could also have a stroke that is less than the gap 110 length, in which case contact between the distal end 100b of the inner tube 100 and the upper inner shoulder 55 of the inner sleeve 40 may not occur.

During extension and retraction of the sample capture element 60, the sample capture element is guided by contact between its exterior surface and the interior surface of the distal portion 40a of the inner sleeve 40, as well as by contact between the exterior surface of the inner tube 10 and the interior surface of the proximal portion 40a of the inner sleeve 40. Proper axial linear movement of the sample capture element 60 is thus ensured.

It may be desirable to prevent rotation of the sample capture element 60 such that repeated orientation of the sample capture pocket 65 during sample capture element extension can be assured. As shown in FIGS. 4a-4b, rotation of the sample capture element 60 of this embodiment of the autosampling device 5 is prevented by causing the ends of the inner tube/sample capture element pin 105 to extend into linearly arranged slots 115 in the proximal portion 40a of the inner sleeve 40 (see FIG. 1). Consequently, the sample capture element 60 is permitted to reciprocate along the longitudinal axis of the autosampling device 5, but is prevented from rotation with respect thereto.

During use of the autosampling device 5, at least the distal end of the protruding outer sleeve 30 is typically immersed in a material from which a sample is to be extracted. The depth of the material need only be sufficient to cover the extended portion of the sample capture element. At the desired time, the actuator 260 is activated to extend the sample capture element 60 as described above. This causes the sample capture element 60 to enter the material to be sampled, whereby an amount of the material fills the sample capture pocket 65 and remains therein as the actuator 260 is subsequently activated to retract the sample capture element back into its closed position.

With the sample of material trapped in the sample capture pocket, the sample may be quenched with a quenching media, as represented in FIG. 4a, so as to halt an ongoing reaction prior to transferring the sample of material to another device or vessel. The sample may also be diluted before subsequent removal from the sample capture pocket. Such operational variations are described in more detail below.

Portions of another exemplary embodiment of a sampling device 150 of the present invention are depicted in FIGS. 6a-8. This sampling device 150 embodiment is similar to the autosampling device 5 described above, but has a fewer number of individual components. Particularly, in this alternative embodiment, the inner and outer sleeves 40, 30 and the adapter 25 of the previously described embodiment are combined into a single end cap/sleeve 155 element (hereinafter "end cap" for brevity).

In this embodiment, a proximal portion 155a of the end cap 155 is provided with external threads 160 that engage internal threads 225 of an outer tube 220. The proximal portion 155a of the end cap 155 is of lesser diameter than a distal portion 155b thereof, which results in the formation of a shoulder 165 slightly distally of the end cap threads 160. When the end cap 155 is threaded into the outer tube 220, the shoulder 160 is brought into contact with the distal end of the outer tube 220 and the end cap is thus secured thereto. The proximal portion 155a of end cap 155 also extends into the interior of the outer tube 220 and may produce sealing contact therewith.

The outer tube 220 may be constructed from various materials depending on the substances to which it might be exposed. In this particular embodiment, the outer tube 220 is again constructed of a HASTELLOY material in similar fashion to the outer tube 10 of the autosampling device 5 of FIGS. 1-5.

The distal portion 155b of the end cap 155 is provided with an axial bore 170, the diameter of which may approximate the outer diameter of a sample capture element 175 that will pass therethrough. Consequently, the bore 170 acts as a reciprocation guide for the sample capture element 175. The interior surface of the bore 170 also seals against the outer surface of the sample capture element 175.

To this end, while the end cap 155 may be constructed from various materials depending on the materials to which it might be exposed, it has been determined that the natural elasticity of PTFE creates a good seal when used to construct the end cap. Particularly, it has been found that the natural elasticity of PTFE allows it to create a good seal with the interior of the outer tube 220, as well as a good seal with the outer surface of the sample capture element 175 while still permitting low-friction reciprocation of the sample capture element in the bore 170 of the end cap 155.

When the end cap 155 is comprised of PTFE or a similar material, the bore therein may be made smaller than the outer diameter of a sample capture element 175 so that when the two components are fitted together the TEFLON yields at the inside bore and burnishes during installation. Preferably, the size of bore in the end cap 155 is selected to provide a compressive sealing force against the sample capture element 175.

For operations at higher temperatures, the end cap 155 may be fitted within a thin metal (e.g., HASTELLOY) sleeve. The sleeve operates to contain expansion of the end cap 155 that results from higher temperatures, thereby maintaining the sealing capabilities of the end cap by balancing the expansive forces with the increased elasticity of the PTFE. This allows the sampling device 150 to be used and cycled at elevated temperatures while still maintaining proper function.

Figure 7:
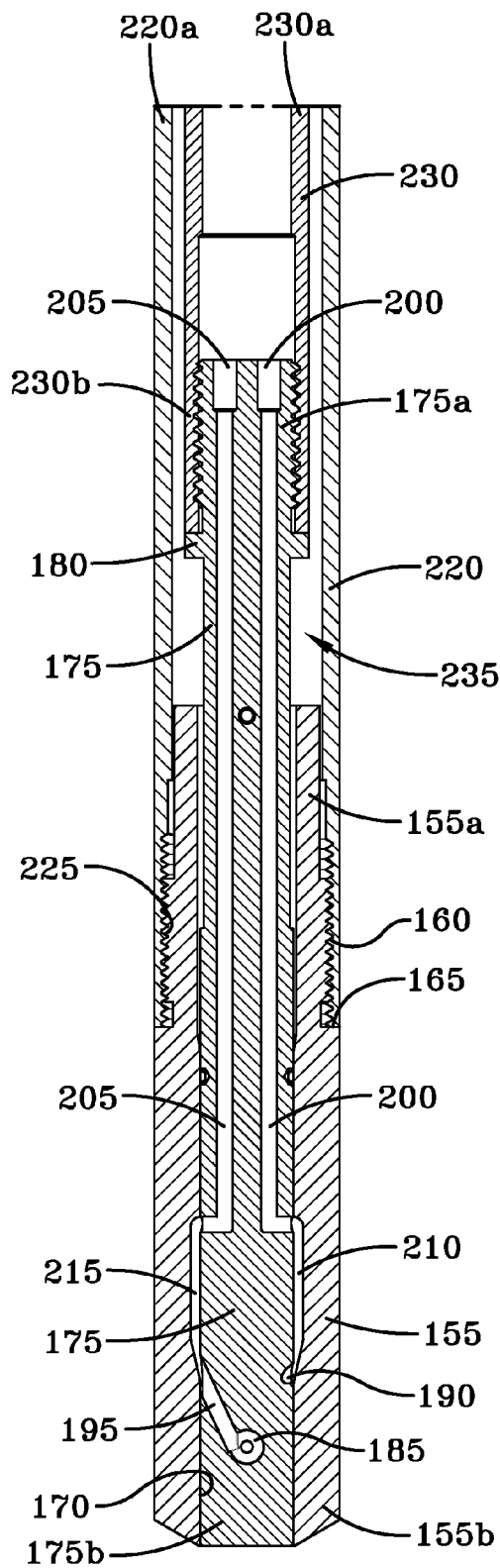
FIG. 7 is a cross-sectional view of the distal portion of the autosampling device shown in FIGS. 5a-5b.

As with the previously described autosampling device 5, this sampling device 150 also includes a sample capture element 175. As described, and as best shown in FIG. 7, the sample capture element 175 is located to reciprocate within the bore 170 of the end cap 155. To that end, the outer diameter of the sample capture element 175 is close in dimension to the inner diameter of the bore 170 in the end cap 155, such that a tight but guided slidable fit is produced therebetween (as described above).

The length of the sample capture element 175 may vary depending on the length of the outer tube 220 and/or other components of the sampling device 150. The length of the sample capture element 175 is at least sufficient to extend beyond the proximal end 155a of the end cap 155 by a distance that is minimally equivalent to the desired sample capture element extension length.

Figure 8:
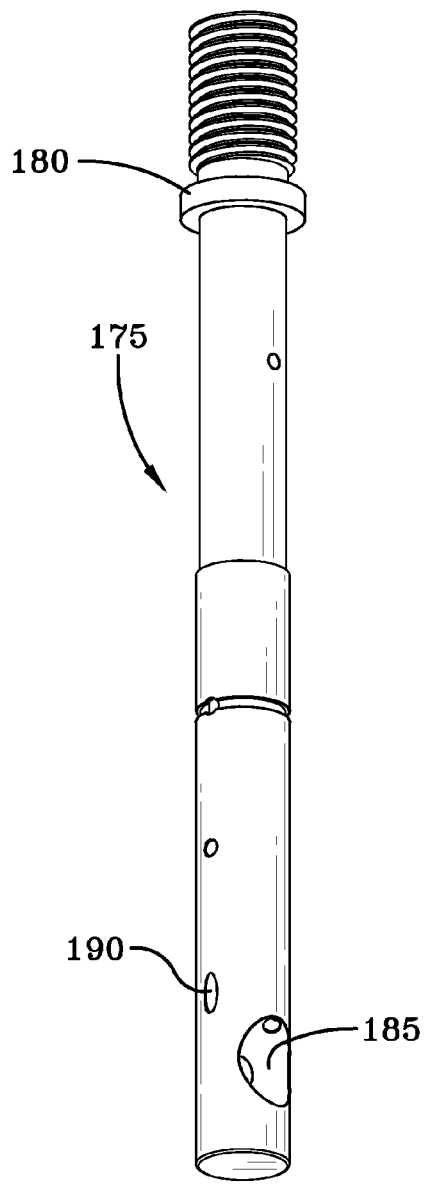
FIG. 8 is an enlarged perspective view of an exemplary sample capture element that may be used with the autosampling device of FIGS. 6a-6b and FIG. 7.

As most clearly shown in FIGS. 7-8, the sample capture element 175 of this embodiment includes an elongate cylindrical body with an externally threaded proximal end 175a. As can be observed in FIG. 7, the threaded proximal end 175a of the sample capture element 175 is received within a like-threaded distal end 230b of a substantially hollow inner tube 230 that is concentrically arranged within the outer tube 220. A collar 180 of enlarged diameter may encircle the exterior of the sample capture element 175 distally of the threads so as to abut the inner tube 230 and permit secure threaded installation of the of the sample capture element 175 thereto. As with the previously described autosampling device 5, the proximal end 230a of the inner tube 230 extends through the proximal end 220a of the outer tube 220 and may be connected in a similar fashion to an actuator (not shown) that provides the desired extension and retraction of the sample capture element 175.

The sample capture element 175 of this embodiment may be constructed of a HASTELLOY material, as described above, but may also be constructed from various other materials depending on the substances to which it might be exposed and as long as the desired fit between cooperating elements is preserved. For example, the sample capture element 175 may also be constructed of certain ceramic materials.

Referring to FIG. 7, it can be observed that when the sample capture element 175 is in a retracted position, a gap 235 exists between the collar 180 of the sample capture element 175 and the proximal end 155a of the end cap 155. The length of this gap 235 again represents the maximum possible length of extension of the sample capture element 175 because, as shown in FIG. 7, contact between the collar 180 and the proximal end 155a of the end cap 155 will function as a hard stop with respect to sample capture element 175 extension. An associated actuator could also have a stroke that is less than the gap 235, in which case contact between the collar 180 and the proximal end 155a of the end cap 155 may not occur.

During extension and retraction of the sample capture element 175, the sample capture element is guided by contact between its exterior surface and the interior surface of the bore 170 in the end cap 155. Proper axial linear movement of the sample capture element 60 is thus ensured. Due to the secure threaded engagement of the sample capture element 175 and the inner tube 230, rotation of the sample capture element 175 is prevented without interfering with the ability of the sample capture element to reciprocate along the longitudinal axis of the sampling device 150.

When the sample capture element 175 is in a retracted (closed) position, as shown in FIGS. 6a and 7, the distal end 175b thereof is preferably positioned substantially evenly with the distal end 155b of the end cap 155. When the sample capture element 175 is in an extended (sampling) position, as shown in FIG. 6b, the distal end 175b thereof protrudes from the distal end 155b of the end cap 155 by some predetermined distance.

As shown in FIGS. 6a, 7 and 8, the sample capture element 175 is again provided with a concave sample capture pocket 185 that operates as described above to capture an amount of a sample in which the distal end of the sampling device 150 is immersed. The sample capture pocket 185 may be provided in different sizes to capture different sample volumes.

The sample capture element 175 is again ported to allow for purging/venting and to allow for quenching of material samples located in the sample capture pocket 185 thereof. To this end, the sample capture pocket 185 is provided with a quench port 190 and a purge/vent port 195, each of which is associated with a corresponding channel 200, 205 that runs through the sample capture element 175 and exits through the proximal end 175a thereof. Porting grooves 210, 215 are provided in the end cap 155 to allow the ports 190, 195 in the sample capture pocket 185 to communicate with the corresponding channels 200, 205 in the sample capture element 175 during a quenching or purge/vent cycle.

As with the autosampling device 5 described above, a by-pass groove 240 may be provided to permit circulation of a quench media while the sample capture element 175 is in an extended position. Also in similar fashion to the autosampling device 5 described above, tubing or similar conduit may be connected to each of the quench and purge/vent channels 200, 205 to lead quench materials to the sample capture pocket 185, and to allow for venting and for material to be purged from the sample capture pocket. Such tubing may again be routed through the inner tube 230 and may be connected to the sample capture element 175 as previously described.

Use of the sampling device 150 occurs generally in the same manner described above with the respect to the autosampling device 5 of FIGS. 1-5. That is, at least the distal end of the end cap 155 is typically immersed in or suspended over a material from which a sample is to be extracted. At the desired time, the actuator (whether powered or hand-actuated) is activated to extend the sample capture element 175 therefrom. This causes the sample capture element 175 to enter the material to be sampled, whereby an amount of the material fills the sample capture pocket 185 and remains therein as the actuator is subsequently activated to retract the sample capture element back into its closed position.

With the sample of material trapped in the sample capture pocket 185, the sample may be processed such as for example, by mixing, by dilution, or by contacting with a quenching substance so as to halt an ongoing reaction prior to transferring the sample of material to another device or vessel. Such operational variations are described in more detail below.

An alternative exemplary embodiment of a sample capture element 300 and an associated sleeve element 345 are depicted in FIGS. 9a-9b and 10a-10b. Such an embodiment may be effective when it is desired or required to construct a sample capture element from a hard material such as a glass or a ceramic. Whereas small holes, channels and other features of a metallic sample capture element may be created by various techniques, including by EDM (electrical discharge machining) techniques, creating such small features in a glass, ceramic, etc., sample capture element may be substantially more difficult, if not impossible. Therefore, it has been found that with a sample capture element made from such hard materials, moving the various passages (conduits) thereof to the outside surface allows the same function to be achieved while simplifying or permitting the necessary machining (or forming). Additionally, attachment of tubing or similar conduit may also be moved to the outside of the sample capture element, where there is more space.

Figure 9A:
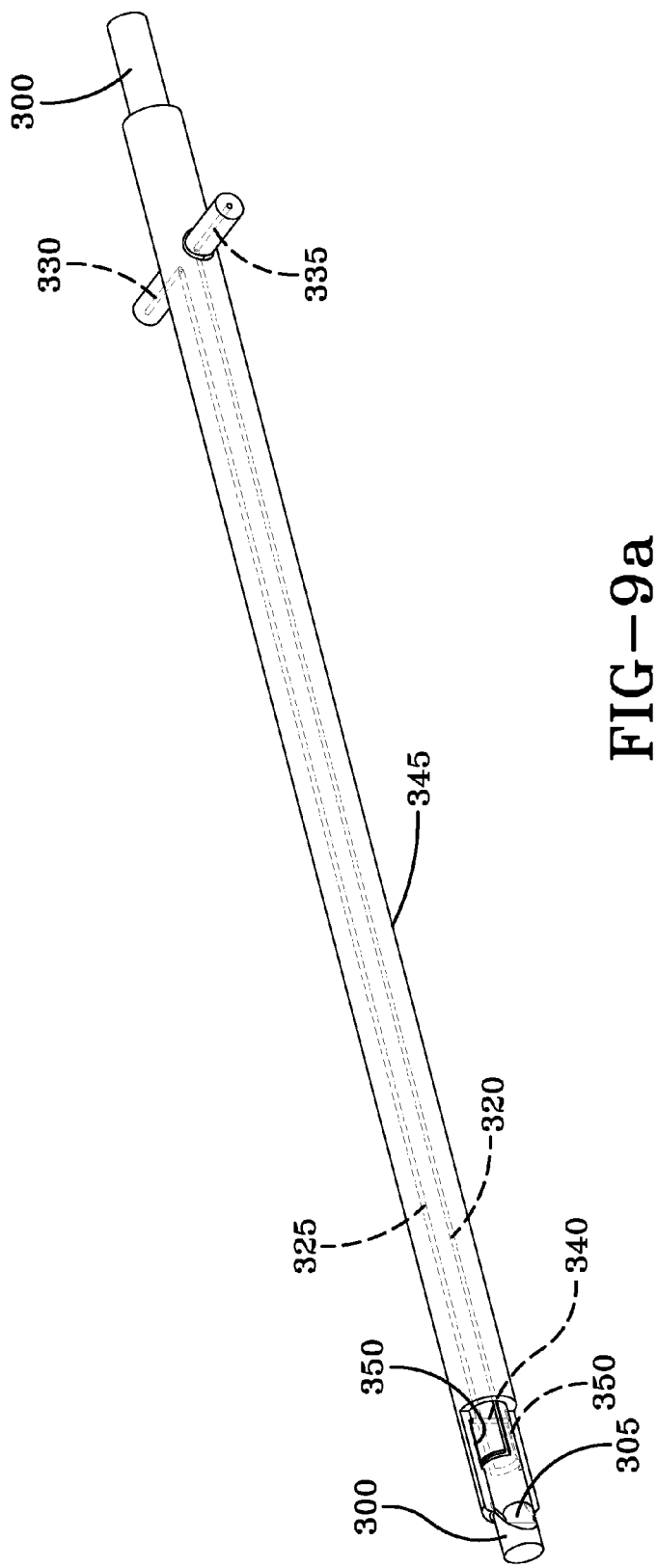
FIG. 9a is a transparent view depicting an alternate embodiment of a sample capture element and associated sleeve of the present invention, with the sample capture element in an extended position.
Figure 9B:
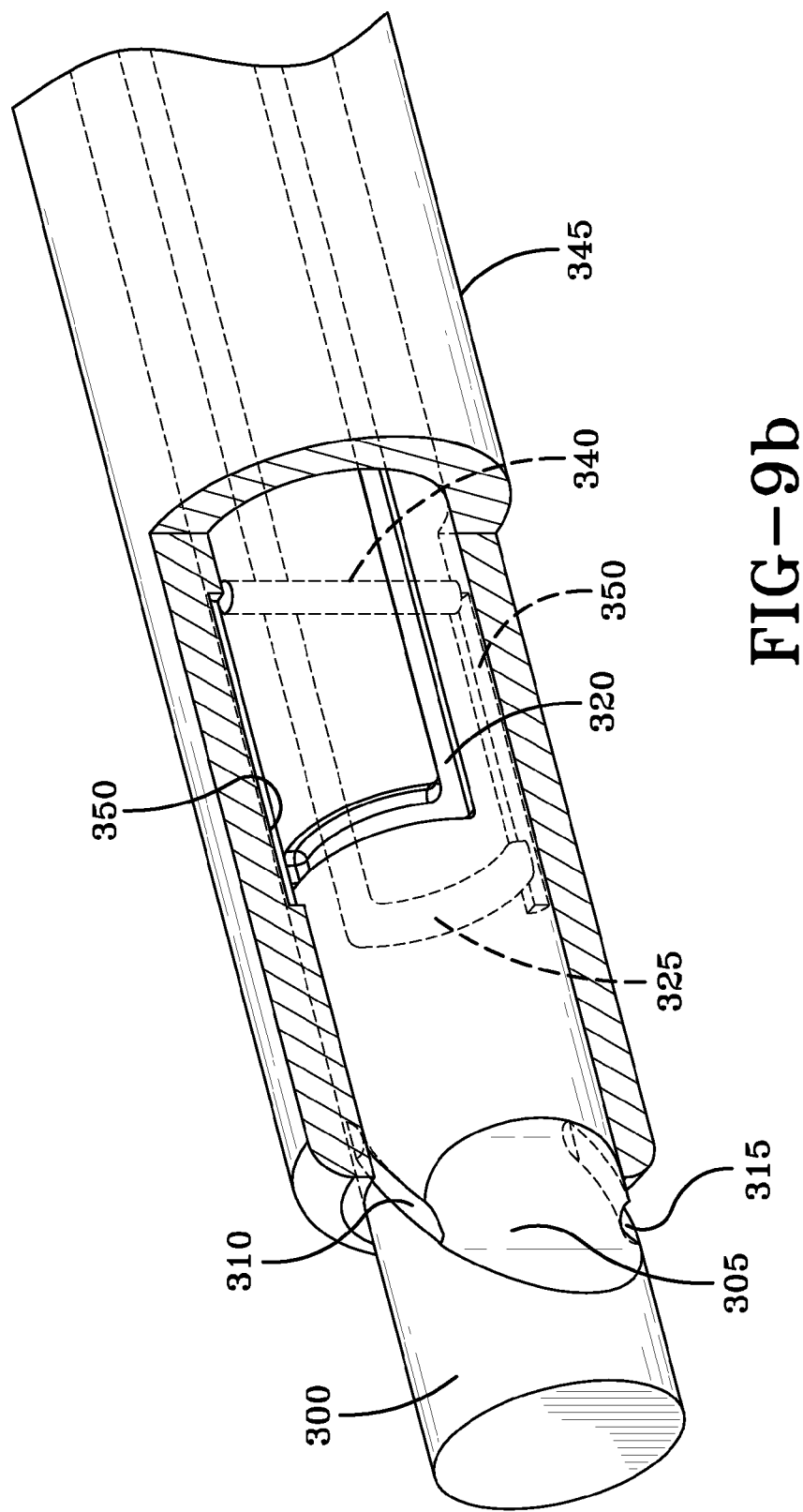
Figure 10A:
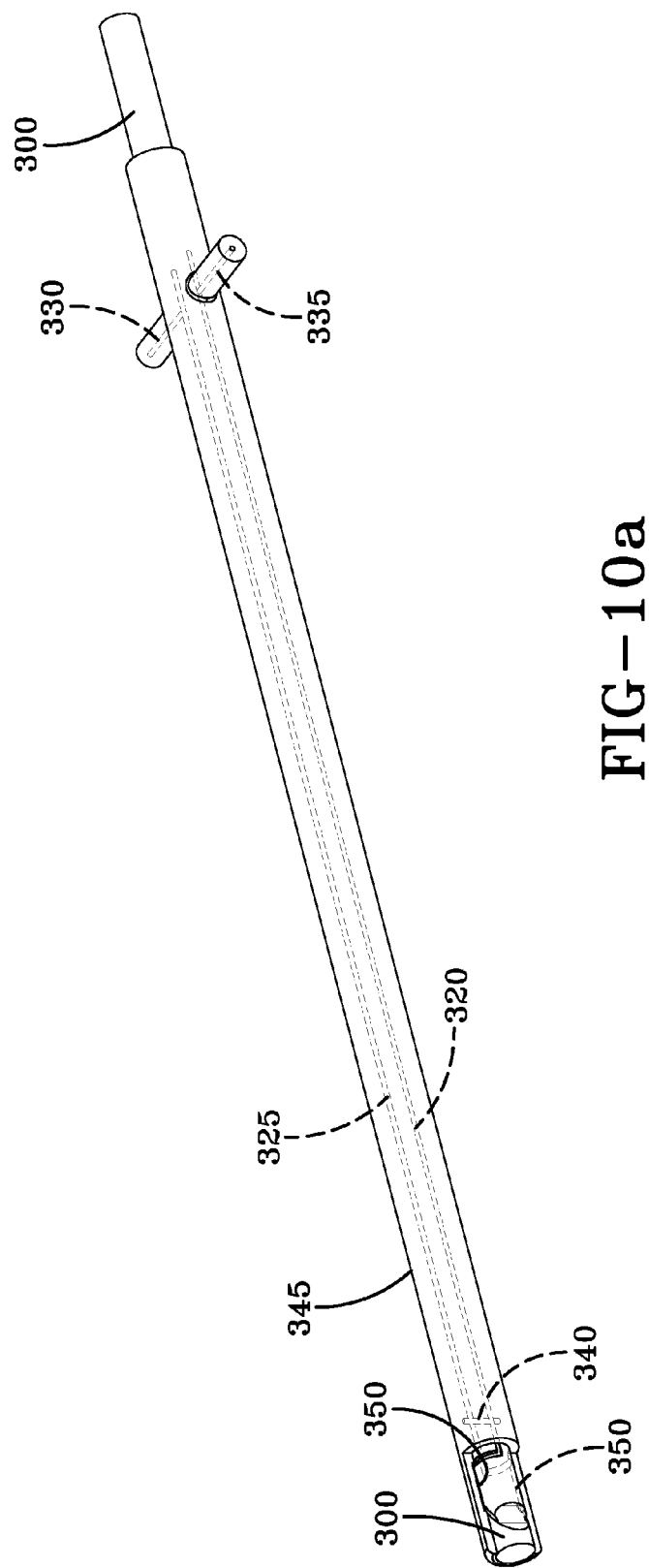
FIG. 10a is a transparent view showing the sample capture element and associated sleeve of FIG. 9a in a retracted position.
Figure 10B:
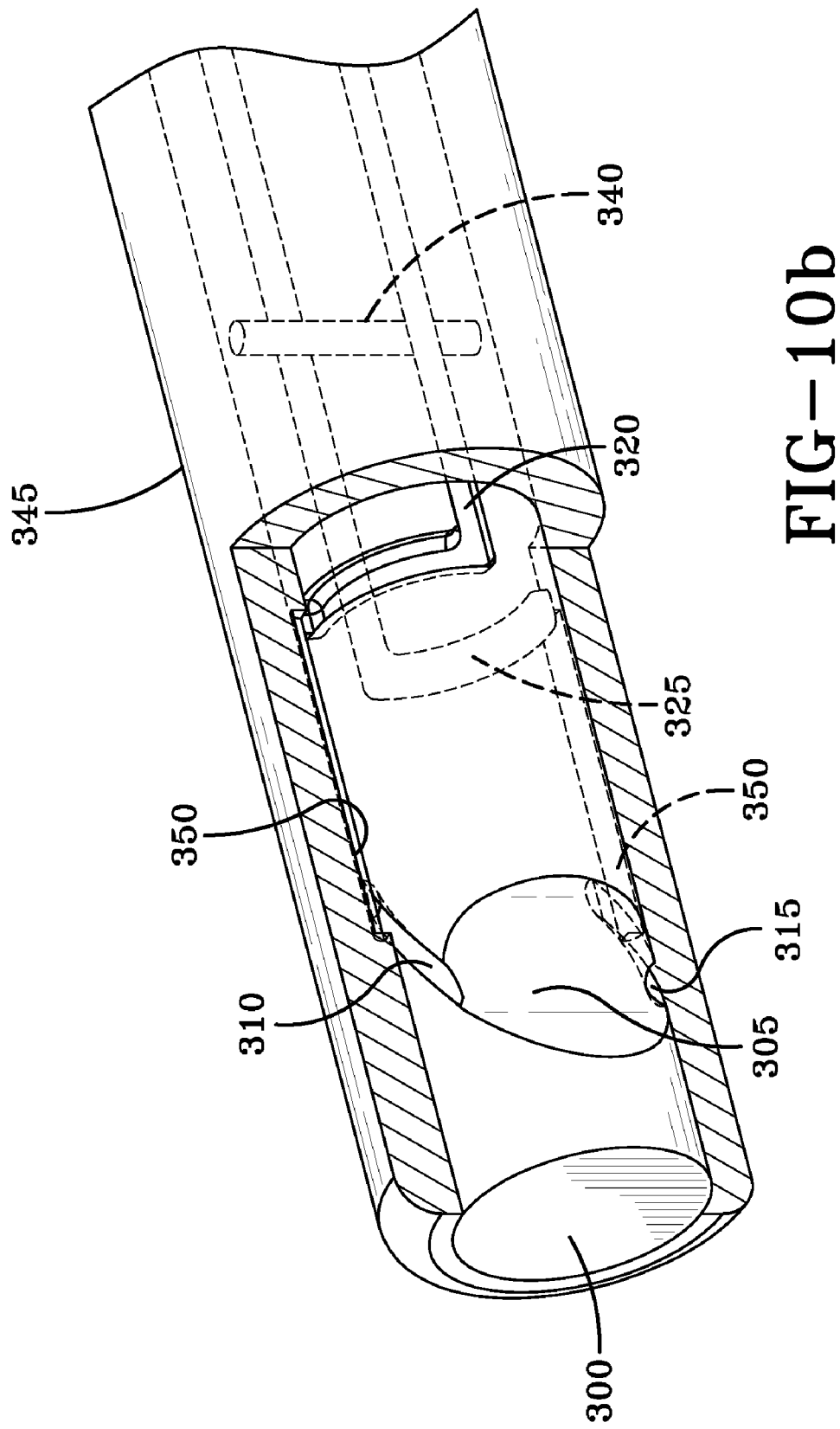

The exemplary embodiment of the sample capture element 300 is shown in an extended position in FIGS. 9a-9b and in a retracted position in FIGS. 10a-10b. Such sample capture element positions will be well-understood by virtue of the previously described exemplary embodiments of the present invention.

As shown, the sample capture element 300 again includes a concave sample capture pocket 305 that, during sample capture element extension, is exposed to and captures an amount of a sample in which the distal end of the sample capture element 300 is immersed. The sample capture pocket 305 may again be provided in different sizes to capture different sample volumes (aliquots).

The sample capture pocket 305 is provided with a quench port 310 and a purge/vent port 315 that, when the sample capture element 300 is in a retracted position, are placed into fluid communication with corresponding conduits 320, 325 that run longitudinally along the exterior surface of the sample capture element 300 and exit into inlet/outlet ports 330, 335 near the proximal end 300a thereof. This fluid communication is described in more detail below.

The sample capture element 300 may also be provided with a by-pass port 340 that permits the supply and possible circulation of a quench media through the conduits 320, 325 while the sample capture element is in an extended position. This quench media supply and/or recirculation is described in more detail below.

The sample capture element 300 is shown to reside and reciprocate within a sleeve 345. As described above with respect to the previously described exemplary embodiments, the sleeve 345 may again be manufactured from a PTFE material, such as TEFLON. The use of other sleeve materials may also be possible depending on the particular material from which the sample capture element 300 is constructed. The outer diameter of the sample capture element 300 and the inner diameter of the sleeve 345 are of a dimension that produces a sealing but guided slidable fit therebetween, such that there is no leakage of fluid from the sample capture element conduits 320, 325.

As can be best observed in FIGS. 9b and 10b, the sleeve 345 is provided with a pair of elongate and axially directed transfer ports 350 that pass through the wall of the sleeve. As described in more detail below, the transfer ports 350 permit fluid communication between the sample capture element conduits 320, 325 and, depending on the position of the sample capture element 300, either the sample capture element by-pass port 340 or the quench port 310 and purge/vent port 315 in the sample capture pocket 305.

The sample capture element 300 is shown in an extended position in FIGS. 9a-9b, wherein the sample capture pocket 305 is exposed for collection of a sample from a material volume into which the sample capture pocket would be immersed. As can be most clearly observed in FIG. 9b, in this position, an arcuate section of each sample capture element conduit 320, 325 is placed in fluid communication with a first end of the transfer ports 350 of the sleeve 345. Simultaneously therewith, the second end of each transfer port 350 is placed in fluid communication with the by-pass port 340 in the sample capture element 300. Consequently, when the sample capture element 300 is in an extended position, a quench media can be supplied thereto and stored or allowed to recirculate through a fluid path defined by the inlet/outlet ports 330, 335, the conduits 320, 325, the transfer ports 350, and the by-pass port 340. Supplying quench media to a sample capture element in this manner has already been generally explained above and, therefore, need not be restated here.

The sample capture element 300 is shown in a retracted position in FIGS. 10a-10b, wherein the sample capture pocket 305 is withdrawn into the sleeve 345 to permit acting on a material sample trapped therein. As can be most clearly observed in FIG. 10b, when the sample capture element 300 is in the retracted position, the arcuate section of each sample capture element conduit 320, 325 is placed in fluid communication with the second end of the sleeve transfer ports 350. Simultaneously therewith, the first ends of the transfer ports 350 are respectively placed into fluid communication with the quench port 310 and purge/vent port 315 in the sample capture pocket 305. Consequently, when the sample capture element 300 is in a retracted position, a sample in the sample capture pocket 305 may be quenched, diluted, and removed therefrom to another vessel or device, and the sample capture pocket may be purged with a gas or another fluid, via a fluid path defined by the inlet/outlet ports 330, 335, the conduits 320, 325, the transfer ports 350, and the quench port 310 and purge/vent port 315. Operational variations are described in more detail below.

In using any of the above-described exemplary embodiments of a sampling device of the present invention, the sampling device may be readied for sampling, such as by first cleaning the sampling lines (tubing) by purging with neutral fluids, gases or an inert gas. It is also possible to draw vacuum prior to purging of the sampling lines. Such cleaning may be performed in a cyclic fashion to ensure that any impurities are removed. Depending on the design of the sampling device, the quench/dilute lines can be pre-flooded with respective fluids.

At an appropriate time, the sample capture element is extended and an aliquot of the reaction mixture is captured by the sample capture pocket. Depending on the material (e.g., the reaction mixture) being sampled, the actual sampling can take place immediately after the sample capture element is extended or with a certain time period thereafter, such that the sample capture pocket may be purged with the reaction mixture prior to taking a sample.

With a sample of material in the sample capture pocket, the sample capture element is then retracted, trapping the sample of material in the sample capture pocket and making it available for immediate processing. Depending on the scheme desired by a user of the sampling device, several actions can subsequently take place. First, the sample of material may be contacted with a quench fluid, upon which the reaction is stopped very quickly, if not immediately. In this case, the sample of material represents the reaction mixture substantially as it existed at the time of sampling. The quenched sample can then be diluted and discharged to a respective analyzer, such as for example, a gas chromatograph, a HPLC, a combination of both, or one or more other suitable analyzers. Under an alternative scheme, the sample may be diluted only, and discharged (e.g., forwarded to an analyzer) as is without first being quenched. Under yet another scheme, the sample is diluted prior to being quenched. While this technique may be less efficient, it may be necessary, for example, in a case where the quench material cannot be solved in the solvent used for the reaction. As a specific example, it would be possible to take a sample from a biologic reaction and use a quench material that is only solvable in a toxic solvent. The steps of quenching and dilution may also be combined in other ways not specifically described herein.

The steps of diluting and discharging a material sample may be accomplished in various ways. For example, a continuous fluid (e.g., a suitable solvent or gas) stream may be used, which stream delivers the material sample to the analyzer. Alternatively, a specified amount of dilution fluid may be cyclically pumped through a concentrated sample and then used for sample discharge. In this technique, the sample will be thoroughly mixed with the dilution fluid. Such a technique may be desirable or necessary, for example, when sampling slurry reaction mixtures. It may also be possible to use a vacuum pump to cause the discharging of a quenched, diluted or unaltered material sample.

Figure 11:
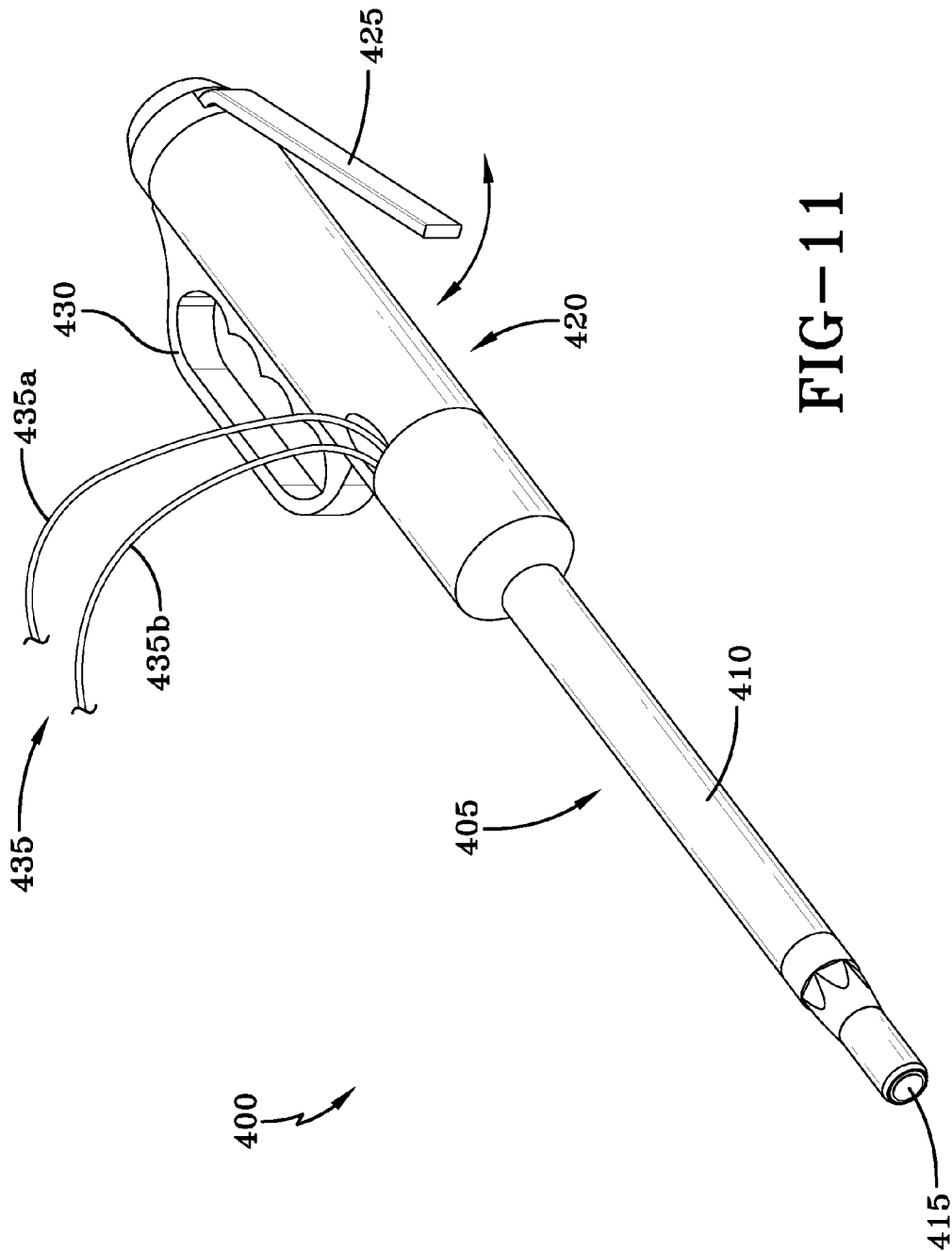
FIG. 11 is an isometric view of one exemplary embodiment of a hand-actuated (manual) sampling device of the present invention.
Figure 12:
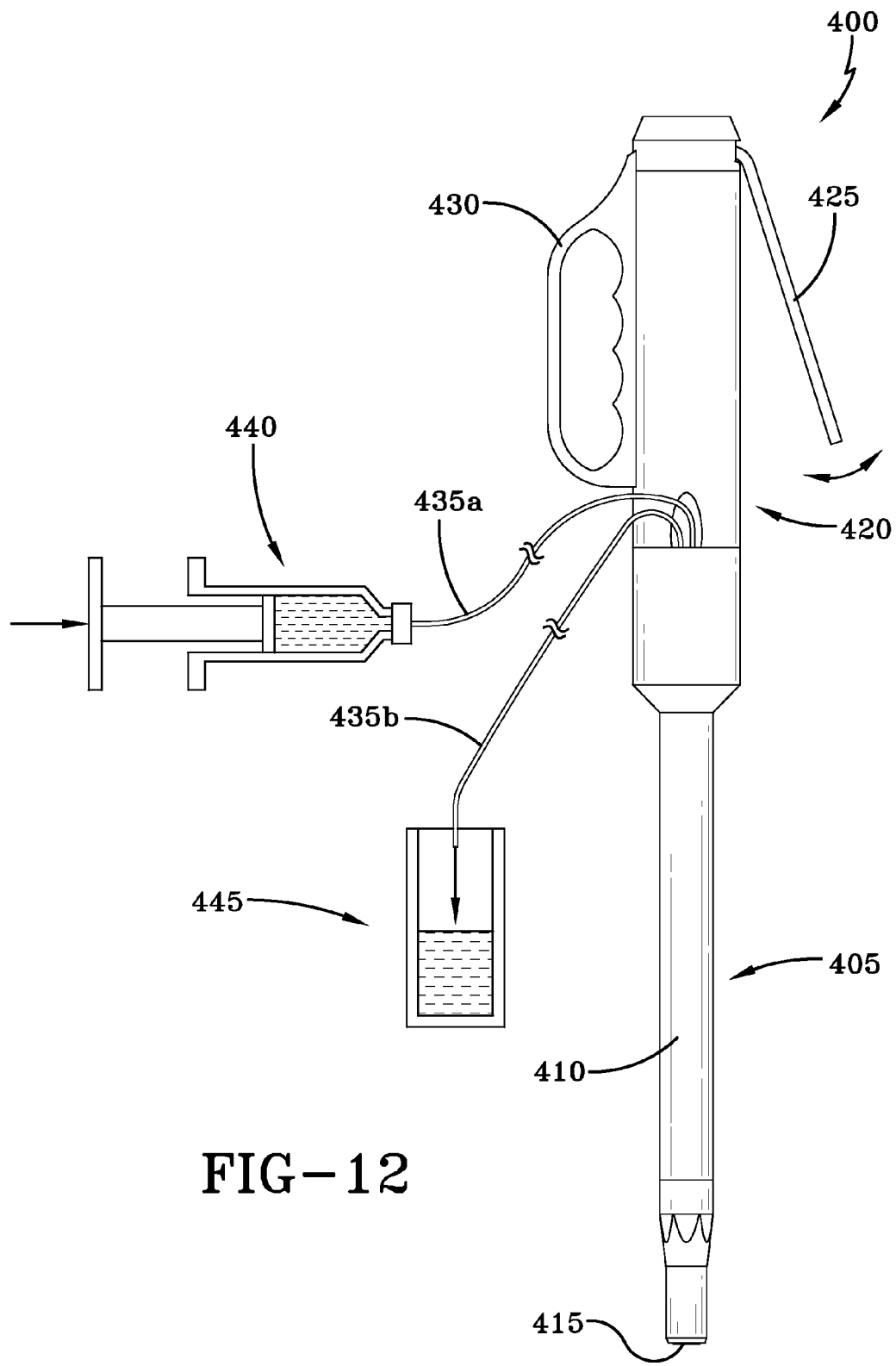
FIG. 12 is a front view of the manual sampling device of FIG. 11 with connections therefrom to a material introduction device and a sample collection vessel schematically represented.

An exemplary hand-actuated (manual) sampling device 400 of the present invention is illustrated in FIGS. 11-12. In a manner similar to that of the previously described sampling devices 5, 150, this manual sampling device 400 also includes a sample capture assembly 405 that includes an outer tube 410 within which is disposed a reciprocative sample capture element 415. While the sample capture assembly 405 is shown herein to be similar in construction to the sample capture assembly 20 of the exemplary embodiment shown in FIG. 1, it is to be understood that a manual sampling device of the present invention may also employ a sample capture assembly of the design described with respect to the sampling device 150, or of a design not specifically shown and described herein.

This manual sampling device 400 also includes a body portion 420 that houses a probe actuator assembly, of which only a lever 425 is visible. As indicated by the arrows, the lever 425 is rotatable between an extended position (as shown) and a position wherein the lever is substantially pressed against the body portion 420 of the device 400. In this particular example, an inward movement of the lever 425 produces an extension of the shape capture element 415. Upon release of the lever 425, a spring or similar mechanism retracts the shape capture element 415 back into the outer tube 410 and returns the lever 425 to its illustrated extended position. Such a mechanism should be well known to one of skill in the art and, therefore, is not described in further detail herein.

In an alternate embodiment of a manual sampling device (not shown), reciprocation of the sample capture element may be accomplished by user actuation of a linear plunger assembly, such as one or more of the plunger assemblies commonly found on commercially available pipettes that would be familiar to one of skill in the art.

The body portion 420 of this embodiment, as well as body portions of other embodiments of a manual sampling device of the present invention, may be provided with a handle 430 or other features that facilitate grasping and/or manipulation by a user. The body portion of a manual sampling device of the present invention may also be shaped or contoured to facilitate grasping and/or manipulation by a user.

As shown, sampling lines 435 protrude from the manual sampling device 400. As can be understood from the foregoing descriptions of other sampling device embodiments 5, 150, such sampling lines 435 are provided to supply processing materials (e.g., quench or dilution media) to the sample capture pocket of the sample capture element 415, and to carry away materials purged from the sample capture pocket.

To this end, a supply sample line 435a is depicted in FIG. 12 as being connected to a processing material supply device 440. In this particular example, the processing material supply device 440 is shown to be a manually operable syringe that can be used to transfer quench, dilution or other sample materials to the sample capture pocket of the device 400 to process a material sample trapped therein. In other embodiments, the syringe may be replaced with another manually operated device or with a powered and possibly automated device, such as a pump.

A purge sample line 435b is depicted in FIG. 12 as being connected to a vessel 445 for receiving material purged from the sample capture pocket of the sampling device 400. The vessel may simply be a container, or may be a receptacle or other receiving element of an analyzer, such as one of the analyzers described above.

While the structure of this manual sampling device 400 differs somewhat from the structure of the autosampling device 5 shown in FIG. 5, the function is still substantially the same. That is, the sample capture element is still extended into a sample of interest at an appropriate time and an aliquot of the sample is captured by the sample capture pocket. With a sample of material in the sample capture pocket, the sample capture element is then retracted, trapping the sample of material in the sample capture pocket and making it available for immediate processing, as described above. Thus, the primary difference between an autosampling device and a manual sampling device of the present invention is simply the fact that the sample capture element of an autosampling embodiment is extended/retracted by a powered actuator (e.g., a pneumatic cylinder), while the sample capture element of a manual sampling embodiment is extended/retracted by operator actuation of a manual actuator (e.g., a lever mechanism or linear plunger assembly).

Figure 13:
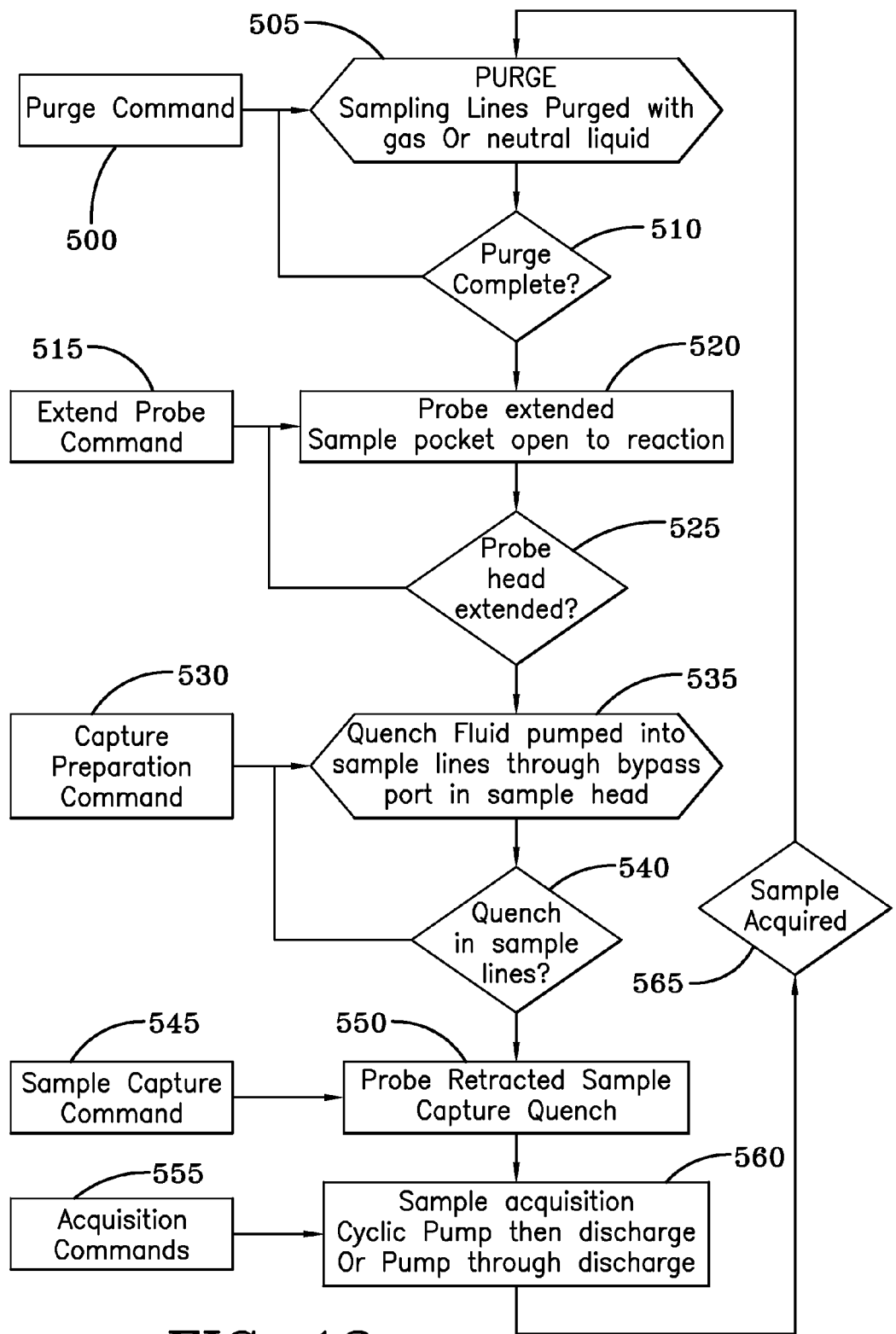
FIG. 13 is a process diagram illustrating one exemplary method of operating an autosampling probe of the present invention.

One specific exemplary method of capturing, processing, and discharging a material sample using an autosampling device of the present invention is diagrammatically illustrated in FIG. 13. In this particular example, a purge command is sent to the autosampling device 500 by a controller in communication therewith. Once this purge command is received, the sampling lines of the autosampling device are purged with a suitable purging material 405, such as a gas or neutral liquid retrieved from a source thereof. The status of the purging operation may be monitored 510. In some cases, this purging step may be skipped during the process of acquiring a material sample.

Once the purging operation has been completed, or in cases where no purging operation is practiced, a probe extend command may be sent 515 to the autosampling device, which causes the sample capture element to extend from the outer tube and the sample capture pocket therein to be exposed to the material of interest 520, as has been described above. The state of sample capture element extension may be monitored 525 to ensure that the sample pocket is fully exposed to the material to be sampled.

In this particular example of autosampling device operation, the captured sample of material will be quenched. Consequently, once the sample capture element has been adequately extended, a capture preparation command may be sent 530 to the autosampling device. In this example, this causes quench fluid to be pumped into the sampling lines 535 of the autosampling device via the by-pass port in the sample capture element. In other examples, wherein a by-pass port is not present, this quenching step may be delayed until after a material sample has been captured and the sample capture element has been retracted. The filling/circulation of the autosampling device sampling lines with quench fluid may be monitored 540 to ensure that quench fluid is available for mixing with a captured sample of material.

Once the quench fluid pumping operation is deemed acceptable, or in cases where a quench fluid pumping operation is delayed (as described above) or where no the quench fluid pumping operation is practiced, a sample capture command may be sent 545 to the autosampling device. This causes the sample capture element of the autosampling device to retract 550 into the outer tube, trapping a sample of material in the sample capture pocket of the sample capture element and causing the material sample to be quenched in situ by the quenching fluid residing in the sample capture element.

A selected acquisition command may subsequently be sent 555 to the autosampling device. This causes the material sample in the sample capture pocket to be acquired (e.g., sent to an appropriate analyzer(s)). In this particular example, acquisition may be accomplished 560 by cyclically pumping a dilution fluid through the material in the sample capture pocket and then discharging the material sample to its next destination, or by using a continuous fluid stream to dilute and discharge the material sample to its next destination. Other dilution/discharge methods and combinations of methods are also possible, as previously described herein.

The sample acquisition process may be monitored for completeness 565. Once sample acquisition is deemed to be complete, the operation may return to the purging stage 500, or may await the next sample capture element extension command if it is desired to skip the purging step or when no purging step is used.

Figure 14:
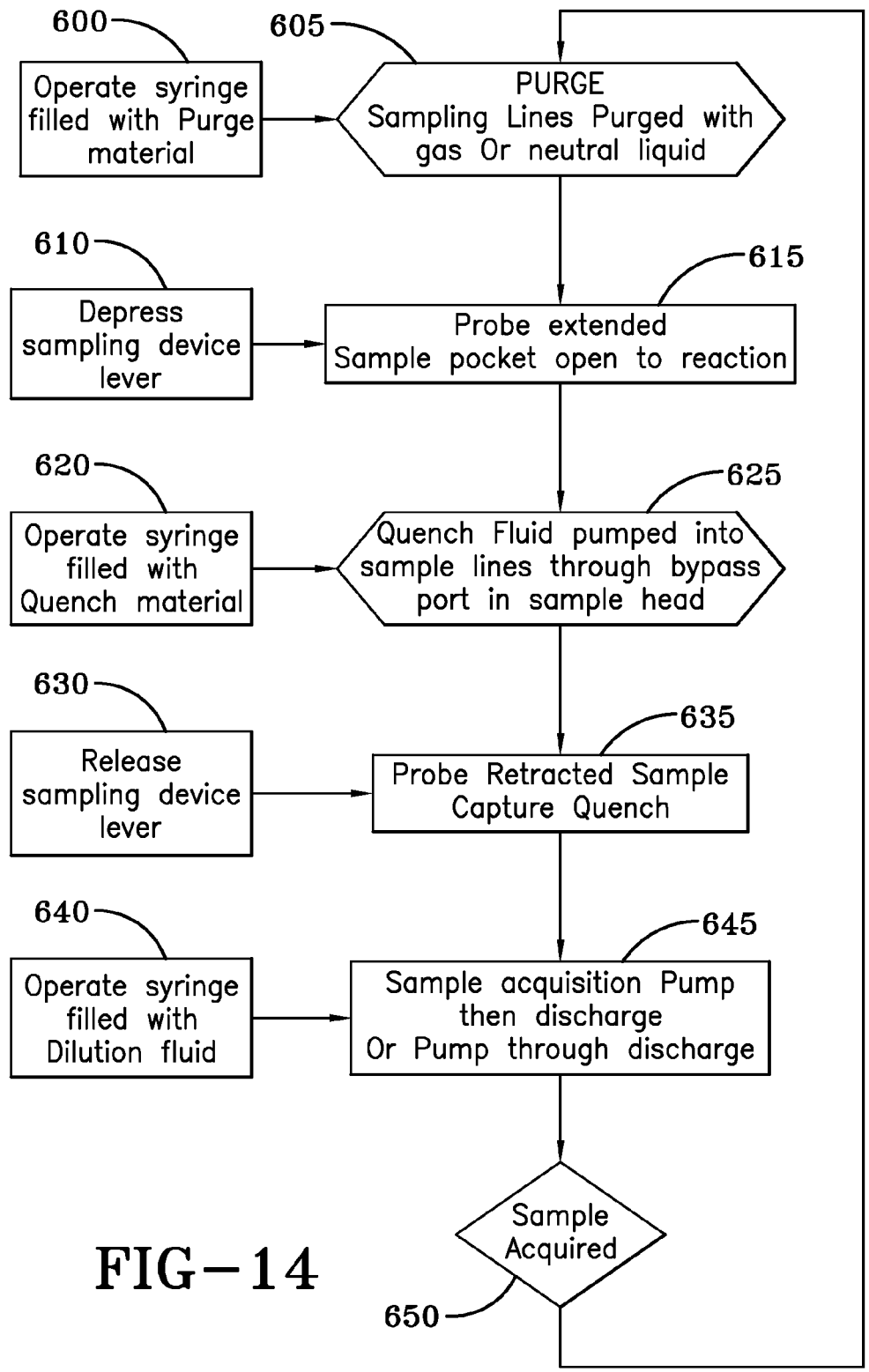
FIG. 14 is a process diagram illustrating one exemplary method of operating a manual sampling probe of the present invention.

An exemplary method of capturing, processing, and discharging a material sample using the manual sampling device of FIGS. 11-12 is diagrammatically illustrated in FIG. 14. In this particular example, the sampling lines of the manual sampling device may be purged 605 with a suitable purging material, such as a gas or neutral liquid, pumped therethrough by appropriate operation 600 of the syringe 440. In some cases, this purging step may be skipped during the process of acquiring a material sample.

Once the purging operation has been completed, or in cases where no purging operation is practiced, the lever 425 of the sampling device 400 is depressed, which causes the sample capture element to extend from the outer tube and the sample capture pocket therein to be exposed to the material of interest 620, as has been described above.

In this particular example of sampling device operation, the captured sample of material will be quenched. Consequently, once the sample capture element has been adequately extended, a syringe 440 is operated 620 to transfer quench fluid under pressure into the sampling lines 635 of the sampling device via the by-pass port in the sample capture element. In other examples, wherein a by-pass port is not present, this quenching step may be delayed until after a material sample has been captured and the sample capture element has been retracted.

Once the quench fluid transfer operation is deemed acceptable, or in cases where a quench fluid transfer operation is delayed (as described above) or where no quench fluid transfer operation is practiced, the lever 425 of the sampling device 400 is released 630. This causes the sample capture element of the sampling device to retract 635 into the outer tube, trapping a sample of material in the sample capture pocket of the sample capture element and causing the material sample to be quenched in situ by the quenching fluid residing in the sample capture element.

With the material sample trapped in the sample capture pocket, a syringe 440 may be used to acquire the sample (e.g., to send the sample to an appropriate vessel, such as the vessel of an analyzer(s)). In this particular example, acquisition is accomplished by operating the syringe 640 to push a dilution fluid through the sample lines and into the material in the sample capture pocket to discharge the material sample to its next destination 645. In an alternate embodiment, a pump or similar device may be used to supply a continuous fluid stream to dilute and discharge the material sample to its next destination. Other dilution/discharge methods and combinations of methods are also possible, as previously described herein.

With the current sample acquired 650, the operation may return to the purging stage, or to the next sample capture element extension step if it is desired to skip the purging step or when no purging step is used.

While certain embodiments of the present invention are described in detail above, the scope of the invention is not to be considered limited by such disclosure, and modifications are possible without departing from the spirit of the invention as evidenced by the following claims:

What is claimed is:

1. A method of capturing a sample of a material of interest, said method comprising:
   providing a sampling device, said sampling device including a reciprocative sample capture element located within an outer tube and adapted for extension and retraction with respect thereto; a sample capture pocket located near a distal end of said sample capture element, said sample capture pocket adapted to capture a volume of material and having a processing material receiving port and a material expulsion port therein, said ports in communication with corresponding channels in said sample capture element when said sample capture element is in a retracted position; and sampling lines leading from said channels in said sample capture element;
   positioning a sampling end of said sampling device in or near a sample of a material of interest;
   causing said sample capture element of said sampling device to extend from said outer tube into said material of interest, thereby filling said sample capture pocket in said sample capture element with an amount of said material;
   causing said sample capture element of said sampling device to retract into said outer tube, thereby trapping a sample of said material of interest in said sample capture pocket;
   processing said sample of material in situ within said sample capture pocket; and
   discharging said sample of material from said sample capture pocket to a downstream location.

2. The method of claim 1, further comprising purging said sampling lines and said sample capture pocket before extending said sample capture element into a material of interest.

3. The method of claim 1, wherein the processing of said sample of material trapped in said sample capture pocket includes quenching said sample by passing a quenching fluid thereto via said processing material receiving port.

4. The method of claim 1, wherein the processing of said sample of material trapped in said sample capture pocket includes diluting said sample by passing a dilution material thereto via said processing material receiving port.

5. The method of claim 4, wherein a specified amount of dilution material is cyclically pumped through said sample of material prior to the discharge of said sample of material by a dilution material.

6. The method of claim 4, wherein a continuous flow of dilution material is used to dilute and discharge said sample of material.

7. The method of claim 4, wherein said dilution material is selected from the group consisting of a gas, a liquid solvent, and a neutral liquid.

8. The method of claim 1, further comprising passing a quenching fluid through said sampling lines of said sampling device while said sample capture element thereof is extended into a material of interest.

9. The method of claim 8, wherein said quenching fluid is circulated through said sampling lines via a by-pass port in said sample capture element.

10. The method of claim 1, further comprising using a vacuum pump to discharge or assist with discharging said sample of material.

11. The method of claim 1, wherein a sample of material is discharged to an analyzer selected from the group consisting of a gas chromatograph, a HPLC device, and a combination thereof.

12. The method of claim 1, wherein said sampling device is an autosampling device, and wherein operating commands are sent to said autosampling device by a microprocessor-based controller associated with another device used to control or analyze a material of interest.

13. The method of claim 12, further comprising monitoring one or more steps of a sample capture operation for completion and awaiting confirmation of completion before proceeding to a subsequent step.

14. The method of claim 1, wherein said sample capture element is extended and retracted by a powered linear actuator.

15. The method of claim 1, wherein said sample capture element is manually extended and retracted by a user of said device.

16. A method of capturing a sample of a material of interest, said method comprising:
   providing an autosampling device, said autosampling device including a reciprocative sample capture element located within an outer tube and adapted for extension and retraction with respect thereto; a sample capture pocket located near a distal end of said sample capture element, said sample capture pocket adapted to capture a volume of material when extended and to trap said volume of material when retracted, said sample capture pocket having a port for receiving processing material therein and a port for expelling material therefrom, said ports in communication with corresponding channels in said sample capture element when said sample capture element is in a retracted position; and sampling lines leading from said channels in said sample capture element;

connecting said autosampling device to an actuator adapted to produce a selective extension and retraction of said sample capture element;

positioning a sampling end of said autosampling device in or over a sample of a material of interest;

activating said actuator to cause said sample capture element of said autosampling device to extend from said outer tube into said material of interest, thereby filling said sample capture pocket in said sample capture element with an amount of said material;

activating said actuator to cause said sample capture element of said autosampling device to retract into said outer tube, thereby trapping a sample of said material of interest in said sample capture pocket;

processing said sample of material in said sample capture pocket by passing a processing material thereto via a sampling line, a corresponding channel in said sample capture element, and a processing material receiving port in said sample capture pocket; and discharging said sample of material from said sample capture pocket to a downstream location via an expulsion port in said sample capture pocket, a corresponding channel in said sample capture element, and a sampling line connected thereto.

17. The method of claim 16, further comprising purging said sampling lines and said sample capture pocket before extending said sample capture element into a material of interest.

18. The method of claim 16, wherein the processing of said sample of material trapped in said sample capture pocket includes quenching said sample by passing a quenching fluid thereto via said processing material receiving port.

19. The method of claim 16, wherein the processing of said sample of material trapped in said sample capture pocket includes diluting said sample by passing a dilution material thereto via said processing material receiving port.

20. The method of claim 19, wherein a specified amount of dilution material is cyclically pumped through said sample of material prior to the discharge of said sample of material by a dilution material.

21. The method of claim 19, wherein a continuous flow of dilution material is used to dilute and discharge said sample of material.

22. The method of claim 19, wherein said dilution material is selected from the group consisting of a gas, a liquid solvent, and a neutral liquid.

23. The method of claim 16, further comprising circulating a quenching fluid through said sampling lines of said sampling device while said sample capture element thereof is extended into a material of interest.

24. The method of claim 23, wherein said quenching fluid is circulated through said sampling lines via a by-pass port in said sample capture element.

25. The method of claim 16, further comprising using a vacuum pump to discharge or assist with discharging said sample of material.

26. The method of claim 1, wherein a sample of material is discharged to an analyzer selected from the group consisting of a gas chromatograph, a HPLC device, and a combination thereof.

27. A sampling device for capturing a sample of a material of interest, said device comprising:
a reciprocative sample capture element located within an outer tube and adapted for extension and retraction with respect thereto;
a sample capture pocket located near a distal end of said sample capture element, said sample capture pocket adapted to capture a volume of material;
a processing material receiving port located in said sample capture pocket;
a material expulsion port located in said sample capture pocket;
corresponding channels in said sample capture element, said channels in communication with said ports when said sample capture element is in a retracted position;
a sampling line leading from a channel in said sample capture element to at least one supply of processing material to supply processing material to said sample capture pocket for the in situ processing of a material sample; and
a sampling line leading from a channel in said sample capture element to at least one downstream vessel for receiving material expelled from said sample capture pocket.

28. The sampling device of claim 27, wherein said channels in said sample capture element are internal thereto.

29. The sampling device of claim 27, wherein said channels in said sample capture element extend along the external surface thereof.

30. The sampling device of claim 27, wherein said device is an autosampling device and said actuator is a powered linear actuator.

31. The sampling device of claim 27, wherein said device is a manual sampling device and said sample capture element is manually extended and retracted by a user of said device.

* * * * *